US011141451B2

(12) United States Patent
Jo et al.

(10) Patent No.: US 11,141,451 B2
(45) Date of Patent: Oct. 12, 2021

(54) PHARMACEUTICAL COMPOSITION AND HEALTH FUNCTIONAL FOOD COMPRISING OAT EXTRACT AVENANTHRAMIDE C OR DERIVATIVE THEREOF AS EFFECTIVE INGREDIENT FOR PREVENTION OR TREATMENT OF NEURODEGENERATIVE DISEASE

(71) Applicants: INDUSTRY FOUNDATION OF CHONNAM NATIONAL UNIVERSITY, Gwangju (KR); REPUBLIC OF KOREA(MANAGEMENT: RURAL DEVELOPMENT ADMINISTRATION), Jeollabuk-do (KR)

(72) Inventors: Ji Hoon Jo, Gwangju (KR); Hyung Seok Kim, Gwangju (KR); Yu Young Lee, Gyeonggi-do (KR)

(73) Assignees: INDUSTRY FOUNDATION OF CHONNAM NATIONAL UNIVERSITY, Gwangju (KR); REPUBLIC OF KOREA (MANAGEMENT: RURAL DEVELOPMENT ADMINISTRATION), Jeollabuk-do (KR)

( * ) Notice: Subject to any disclaimer, the term of this patent is extended or adjusted under 35 U.S.C. 154(b) by 114 days.

(21) Appl. No.: 16/095,447

(22) PCT Filed: Jul. 4, 2016

(86) PCT No.: PCT/KR2016/007196
§ 371 (c)(1),
(2) Date: Oct. 22, 2018

(87) PCT Pub. No.: WO2017/183768
PCT Pub. Date: Oct. 26, 2017

(65) Prior Publication Data
US 2019/0125819 A1 May 2, 2019

(30) Foreign Application Priority Data

Apr. 20, 2016 (KR) .......... 10-2016-0048134
May 31, 2016 (KR) .......... 10-2016-0066932

(51) Int. Cl.
| | |
|---|---|
| A61K 36/899 | (2006.01) |
| A61K 36/00 | (2006.01) |
| A61K 31/196 | (2006.01) |
| A61K 31/216 | (2006.01) |
| A23L 33/105 | (2016.01) |
| A61P 25/28 | (2006.01) |
| A61K 9/00 | (2006.01) |

(52) U.S. Cl.
CPC .......... *A61K 36/899* (2013.01); *A23L 33/105* (2016.08); *A61K 9/0014* (2013.01); *A61K 9/0019* (2013.01); *A61K 9/0043* (2013.01); *A61K 31/196* (2013.01); *A61K 31/216* (2013.01); *A61P 25/28* (2018.01); *A23V 2002/00* (2013.01); *A23V 2200/322* (2013.01); *A23V 2250/21* (2013.01)

(58) Field of Classification Search
None
See application file for complete search history.

(56) References Cited

U.S. PATENT DOCUMENTS

| | | | | |
|---|---|---|---|---|
| 5,762,953 | A * | 6/1998 | Venkateshwaran | .......................... A61K 9/7084 424/448 |
| 2004/0253647 | A1* | 12/2004 | Mathews | ................ A61P 25/16 435/7.2 |
| 2007/0254055 | A1* | 11/2007 | Meydani | ................... A61P 1/00 424/776 |
| 2011/0112187 | A1 | 5/2011 | Schneider et al. | |
| 2012/0082740 | A1 | 4/2012 | Collins et al. | |

FOREIGN PATENT DOCUMENTS

| | | |
|---|---|---|
| KR | 10-2006-0080122 A | 7/2006 |
| KR | 10-2009-0004706 A | 1/2009 |
| KR | 10-2015-0034024 A | 4/2015 |

OTHER PUBLICATIONS

Vickers (A Vaccine Against Alzheimer's Disease, Drug Aging 2002: 19(2) 487-494) (Year: 2002).*
International Search Report for PCT/KR2016/007196 dated Feb. 20, 2017.
Cha, Won Jun: "JNU Tech Fair, Excellent Technique in Medical Field", Medical Newspaper, Retrieved from the Internet <URL:http://bealth.cbosun.com/news/dailynews_view.jsp?mn_idx=125130>, 2017 (English machine translation is submitted herewith.)
Nie, L. et al., "Mechanism by which Avenanthramide-c, a Polyphenol of Oats, Blocks Cell Cycle Progression in Vascular Smooth Muscle Cells", Free Radical Biology & Medicine, vol. 41, No. 5, pp. 702-708, 2006.
Blennow K et al., "Alzheimer's disease", Lancet, vol. 368, pp. 387-403, 2006 (English Abstract is submitted herewith.)
Christopher R. Connors et al., "Tranilast Binds to Aβ Monomers and Promotes Aβ Fibrillation", Biochemistry, vol. 52 (23), pp. 3995-4002, 2013.

(Continued)

*Primary Examiner* — Michael Barker
*Assistant Examiner* — Randall O Winston
(74) *Attorney, Agent, or Firm* — The PL Law Group, PLLC

(57) ABSTRACT

A pharmaceutical composition and a health functional food including an oat extract as an effective ingredient for prevention or treatment of neurodegenerative disease. More specifically, the present invention provides a pharmaceutical composition and a health functional food including an oat extract such as avenanthramide C or a derivative thereof, for example, avenanthramide methyl ester as an effective ingredient for prevention or treatment of Alzheimer's disease.

10 Claims, 28 Drawing Sheets

(56) References Cited

OTHER PUBLICATIONS

Office action dated Jul. 19, 2016 from Korean Patent Office in a counterpart Korean Patent Application No. 10-2016-0066932 (all the cited references are listed in this IDS.) (English translation is submitted herewith.)

Notice of Allowance dated Apr. 19, 2017 from Korean Patent Office in a counterpart Korean Patent Application No. 10-2016-0066932 (all the cited references are listed in this IDS.) (English translation is submitted herewith.)

* cited by examiner

PHARMACEUTICAL COMPOSITION AND HEALTH FUNCTIONAL FOOD COMPRISING OAT EXTRACT AVENANTHRAMIDE C OR DERIVATIVE THEREOF AS EFFECTIVE INGREDIENT FOR PREVENTION OR TREATMENT OF NEURODEGENERATIVE DISEASE

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2016/007196, filed Jul. 4, 2016, which claims priority to the benefit of Korean Patent Application No. 10-2016-0048134 filed on Apr. 20, 2016 and 10-2016-0066932 filed on May 31, 2016 in the Korean Intellectual Property Office, the entire contents of which are incorporated herein by reference.

TECHNICAL FIELD

The present invention relates to a pharmaceutical composition and a health functional food including an oat extract as an effective ingredient for prevention or treatment of neurodegenerative disease. More specifically, the present invention relates to a pharmaceutical composition and a health functional food including an oat extract such as avenanthramide C or a derivative thereof, for example, avenanthramide methyl ester as an effective ingredient for prevention or treatment of Alzheimer's disease.

BACKGROUND ART

Alzheimer's disease is one of neurodegenerative diseases that cause memory, thinking and behavioral problems, and is estimated to account for 60 to 80% of cases of dementia (Blennow et al., 2006, Lancet 368: 387). Histopathologically, Alzheimer's disease causes general atrophy of a brain, enlargement of a ventricle, multiple lesions of nerve fibers (nerve fiber twist) and neuritic plaques. Several Alzheimer's disease onset modes have been reported, but an onset due to an accumulation of amyloid-β proteins has been reported as the most likely cause. Accumulation of amyloid-β proteins causes damage to nerve cells, and activates a GSK3β enzyme, which is known to interrupt long-term potentiation (LTP) required for memory formation. A period from the onset of Alzheimer's disease to death is usually about 6 to 8 years, but it may be over 20 years.

It is known that 5 million or more people have Alzheimer's disease in the United States. As a proportion of people over 65 years old in the United States continues to increase, the number of Americans with Alzheimer's disease and other dementia is expected to increase annually. In 2000, the elderly population over 65 years old exceeded 7.2% of the total population in Korea, thus indicating that Korea has become an aging society. Therefore, in Korea, the elderly population will account for 11% of the total population in 2010, and thereby the number of patients with dementia is expected to increase. In fact, in the National Dementia Epidemiologic Survey conducted by the Ministry of Korean Health and Welfare in 2012, an incidence of dementia among elderly people over 65 years old was estimated at 540,755, which is 9.18 per 100 persons, and dementia caused by Alzheimer's disease accounted for 70.5%. This is a higher level than 50 to 70% of dementia patients with Alzheimer's surveyed in foreign previous studies. Therefore, it is suggested that treatment of Alzheimer's disease is becoming an important issue to be solved in association with the increase of the elderly population in the future.

SUMMARY

Accordingly, the present inventors have made efforts to develop a composition for prevention or treatment of the neurodegenerative disease using natural products, and consequently, have found that among oat extracts, avenanthramide C or a derivative thereof such as avenanthramide C methyl ester inhibits an activity of glycogen synthase kinase-3β (GSK3β), which is activated by amyloid-β (Aβ), and interrupts an action of amyloid-β which inhibits LTP, and have completed the present invention on the basis of the finding.

It is presumed that "oat" used herein has spread from the East to Central Europe, along with barley, since about 5000 BC. Oat has been used for at least 800 years in Europe for nutritional and medical purposes. Oatmeal is known as a biennial edible plant crop of oats in mono-cotyledonous Gramineae poales, which includes about 70 species, however, only a few of them are grown commercially. Mostly, wild oat (*Avena sativa* L.) species are cultivated, wherein a height is about 90 cm, a leaf length ranges from 15 to 30 cm, a width ranges from 6 to 12 mm, and a sheath leaf is long while a ligule is short and finely split. Flowers bloom in May to June and are panicles, and branches have a whorled arrangement and become split again. Oat glumes do not have a ridge line but include lots of veins and spread out on both sides. Oat aristae are wrapped with inner and outer awns, have hair and include grooves on one side thereof. Fruits are processed into oatmeal and eaten, and generally used to make alcohol, and for raw materials for confectionery and livestock feeds. As components of the oats are beta-carotene, vitamin C, niacin, riboflavin, thiamine, retinol, dietary fiber, and avenanthramide, and the like. Among these, avenanthramide is known as an antioxidant agent to inhibit active oxygen. The avenanthramide may be classified into avenanthramide A, avenanthramide B, avenanthramide C, avenanthramide 0, and avenanthramide P.

As used herein, the term "neurodegenerative disease" refers to a disease in which the nervous system loses functions due to a degenerative change in neuronal cells. The neurodegenerative disease may be selected from the group consisting of Alzheimer's disease, frontotemporal dementia, dementia with Lewy bodies, corticobasal degeneration, Parkinson's disease, multiple system atrophy, progressive supranuclear palsy, Huntington's disease, dentatorubro-pallido-luysian atrophy, spinocerebellar ataxia, amyotrophic lateral sclerosis, primary lateral sclerosis and spinal muscular atrophy, but it is not limited thereto.

As used herein, the term "Alzheimer's disease" is a disease in which losses of significant memory and other intellectual abilities occur enough to hinder patient's daily life, and means a neurodegenerative disease characterized by a histopathological overall atrophy of the brain, enlargement of the ventricle, multiple lesions of nerve fibers (nerve fiber twist), neuritic plaque and the like.

As used herein, the term "amyloid-β" is a peptide including 36 to 43 amino acids, and is produced by degradation of an amyloid precursor protein (APP) by an enzyme such as a secretase. The resulting amyloid-β forms in several forms as it agglomerates. Among them, plaques having neurotoxicity are generated by multimers collapsed in an erroneous form, thereby causing neurological diseases.

As used herein, the term "GSK3β" refers to an enzyme that phosphorylates other proteins and has a role of regulating various actions such as energy metabolism, cell proliferation, apoptosis and the like.

As used herein, the term "long-term potentiation" refers to a phenomenon in which signal transmission between two neurons is continuously improved by simultaneously stimulating the neurons. The long-term potentiation is considered to be one of the major cytological mechanisms in learning and memory. Forming the long-term potentiation strengthens a synapse between the neurons by new protein synthesis, thereby resulting in an increase in abilities of presynaptic neurons and postsynaptic neurons to transmit signals through the strengthened synapse. The long-term potentiation applies to a wide variety of learning from classical conditioning to complex higher cognitive functions.

According to an aspect of the present invention, there is provided a pharmaceutical composition which includes an oat extract as an effective ingredient for prevention or treatment of the neurodegenerative disease. The oat extract may include avenanthramide C represented by Formula 1 below or a derivative thereof:

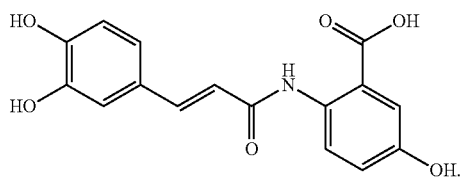

[Formula 1]

In the pharmaceutical composition for prevention or treatment of the neurodegenerative disease according to the present invention, the derivative of avenanthramide C may be avenanthramide C methyl ester represented by Formula 2 below:

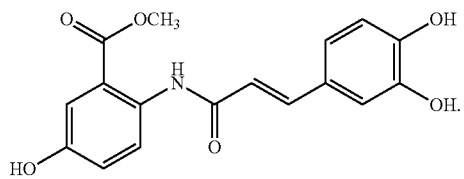

[Formula 2]

In the pharmaceutical composition for prevention or treatment of the neurodegenerative disease according to the present invention, the oat extract may be included in an amount of 50 μM or more.

In the pharmaceutical composition for prevention or treatment of the neurodegenerative disease according to the present invention, the oat extract may inhibit an activity of glycogen synthase kinase-3β (GSK3β) induced by the accumulation of amyloid-β.

In the pharmaceutical composition for prevention or treatment of the neurodegenerative disease according to the present invention, the oat extract may re-induce long-term potentiation (LTP) inhibited by the accumulation of amyloid-β.

The pharmaceutical composition according to the present invention may further include a pharmaceutically acceptable carrier. The pharmaceutically acceptable carrier may include, as those commonly used in the art, lactose, dextrose, sucrose, sorbitol, mannitol, starch, acacia rubber, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, mineral oil, and the like, but it is not limited thereto. The pharmaceutical composition of the present invention may further include lubricants, wetting agents, sweeteners, flavoring agents, emulsifiers, suspensions, preserving agents, and the like, in addition to the above components. Suitable pharmaceutically acceptable carriers and formulations are described in detail in Remington's Pharmaceutical Sciences (19th ed., 1995).

The pharmaceutical composition according to the present invention may be administered orally or parenterally. In a case of parenteral administration, the pharmaceutical composition may be administered by intravenous injection, subcutaneous injection, intramuscular injection, intraperitoneal injection, local administration, dermal administration, nasal administration and the like. Most preferably, the pharmaceutical composition is administered by nasal administration.

A suitable dosage of the pharmaceutical composition according to the present invention may be variously prescribed depending on factors such as a formulation method, an age, body weight, sex, or morbid condition, food, administration time, administration route, excretion rate and reaction sensitivity of the patient. Meanwhile, when using the pharmaceutical composition of the present invention as a composition for nasal administration, a preferred unit-dose spray amount is 20 to 500 μg, and the most preferred unit-dose spray amount is 50 to 200 μg. If the unit-dose spray amount is less than 20 μg, the used amount of the composition is small, thus it is difficult to obtain a desired effect. If the unit-dose spray amount exceeds 500 μg, the composition during nasal spray may flow down from a nasal cavity, making it difficult to administer.

The pharmaceutical composition according to the present invention may be manufactured in a unit dosage form, by formulating using the pharmaceutically acceptable carrier and/or excipient according to a method that can be easily executed by persons having ordinary skill in the art to which the present invention pertains.

According to another aspect of the present invention, there is provided a health functional food which includes an oat extract as an effective ingredient for prevention or improvement of neurodegenerative disease. The oat extract may include avenanthramide C represented by Formula 1 below or a derivative thereof:

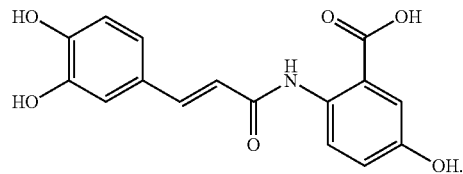

[Formula 1]

In the health functional food for prevention or improvement of the neurodegenerative disease according to the present invention, the derivative of avenanthramide C may be avenanthramide C methyl ester represented by Formula 2 below:

[Formula 2]

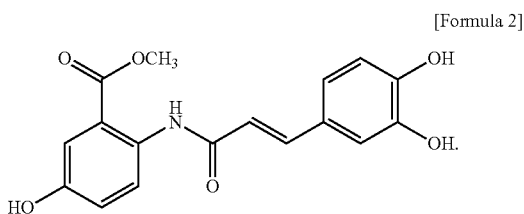 [SMILES: COC(=O)c1cc(O)ccc1NC(=O)/C=C/c1ccc(O)c(O)c1]

In the health functional food for prevention or improvement of the neurodegenerative disease according to the present invention, the derivative of avenanthramide C may include avenanthramide C methyl ester, avenanthramide A or avenanthramide B.

The health functional food according to the present invention includes not only the effective ingredient but also components commonly added during manufacturing food, and may include, for example, proteins, carbohydrates, fats, nutrients, seasoning agents and flavoring agents. The carbohydrate may include: for example, saccharides such as monosaccharides such as glucose, and fructose, etc.; disaccharides such as maltose, sucrose, and oligosaccharides, etc.; polysaccharides such as dextrin, and cyclodextrin, etc.; and sugar alcohols such as xylitol, sorbitol, and erythritol, etc. As the flavoring agent, natural flavoring agents such as thaumatin and *stevia* leaf extract (e.g., rebaudioside A, and glycyrrhizin, etc.) and synthetic flavoring agents (e.g., saccharin, and aspartame, etc.) may be used. For example, when manufacturing the health functional food of the present invention as a health drink, the health functional food according to the present invention may further include citric acid, fructose, sugar, glucose, acetic acid, malic acid, juice, Eucommia extract, jujube extract, licorice extract, and the like, in addition to the effective ingredient of the present invention.

The avenanthramide C, which is the oat extract according to the present invention, is effective in inhibiting the activity of GSK3β induced by amyloid-β, and inducing LTP inhibited by the accumulation of amyloid-β, and thus may be helpfully used in the prevention or improvement of neurodegenerative disease. In particular, the oat extract according to the present invention is a natural product and has stability without cytotoxicity. Therefore, the composition of the present invention including the oat extract as an effective ingredient has an advantage that it is safe for using for a long-term period without having an adverse effect on the human body.

BRIEF DESCRIPTION OF THE DRAWINGS

(FIG. 12A: avenanthramide C-untreated hippocampal fragment, and FIG. 12B: avenanthramide C-treated hippocampal fragment).

DETAILED DESCRIPTION

Hereinafter, the present invention will be described in detail with reference to the following examples. However, the following examples are illustrative of the present invention, and contents of the present invention are not limited by the following examples.

EXAMPLE

Example 1. Preparation of Experimental Animals

C57BL/6 mice (Central Lab. Animal Inc.) and 5×FAD mice (Jackson Laboratory) were prepared. The mice were allowed to freely eat diets and drinking water in a controlled room at a temperature of 23±3° C., humidity of 60±10%, and light/dark cycle of 12 hours, and were adapted for 7 days after delivery and used for the experiment. The management, maintenance and experimental procedures of the experimental animals were carried out under an approval of the Experimental Animal Ethics Committee of Chonnam National University in Korea.

Example 2. Preparation of Hippocampal Slice

The mice of Example 1 were anesthetized and decapitated to excise brains. The extracted brains were kept in a cooled artificial cerebrospinal fluid (aCSF) (124 mM NaCl, 3 mM KCl, 26 mM NaHCO$_3$, 2 mM CaCl$_2$, 1 mM MgSO$_4$, 10 mM Glucose, 1.25 mM NaH$_2$PO$_4$, and 2 mM CaCl$_2$) saturated with 95% oxygen. Hippocampal slices were sampled from the brains, and the hippocampal slice samples were prepared with a thickness of 400 μm. Then, the hippocampal slice samples were recovered in the aCSF (124 mM NaCl, 3 mM KCl, 26 mM NaHCO$_3$, 2 mM CaCl$_2$, 1 mM MgSO$_4$, 10 mM Glucose, 1.25 mM NaH$_2$PO$_4$, and 2 mM CaCl$_2$) saturated with 95% oxygen at a temperature of 22 to 25° C. for 1 hour, and then used in the experiment.

EXPERIMENTAL EXAMPLE

Experimental Example 1. Comparison of Long-Term Potentiation (LTP) Depending on Treatment with Avenanthramide C According to the Present Invention A hippocampal slice of a 4-month-old C57BL/6 mouse was treated with amyloid-β and avenanthramide C two hours before the experiment in amounts as illustrated in Table 1 below, and an LTP comparison experiment was performed.

TABLE 1

| No. | Amyloid-β | Avenanthramide C |
|---|---|---|
| Sample 1 | — | — |
| Sample 2 | 500 nM | — |
| Sample 3 | 500 nM | 50 μM |

TABLE 1-continued

| No. | Amyloid-β | Avenanthramide C |
|---|---|---|
| Sample 4 | — | 50 μM |
| Sample 5 | 500 nM | 10 μM |
| Sample 6 | — | 500 μM |
| Sample 7 | 500 nM | 500 μM |

For LTP induction, the hippocampal slice samples were located in a recording chamber, respectively, and then were observed by analyzing a field excitatory postsynaptic potential (fEPSP) by stimulation of Schaffer-Collateral fiber, while applying stimulations to the samples with 100 Hz every 200 ms, and the experiment was performed for 90 minutes. During the experiment, the aCSF was supplied by flowing with a rate of 2 to 3 ml/min at 30° C., and the obtained experimental results were compared using the ANOVA test known in the art. The obtained results are illustrated in FIGS. 1 to 7.

Figure 1:
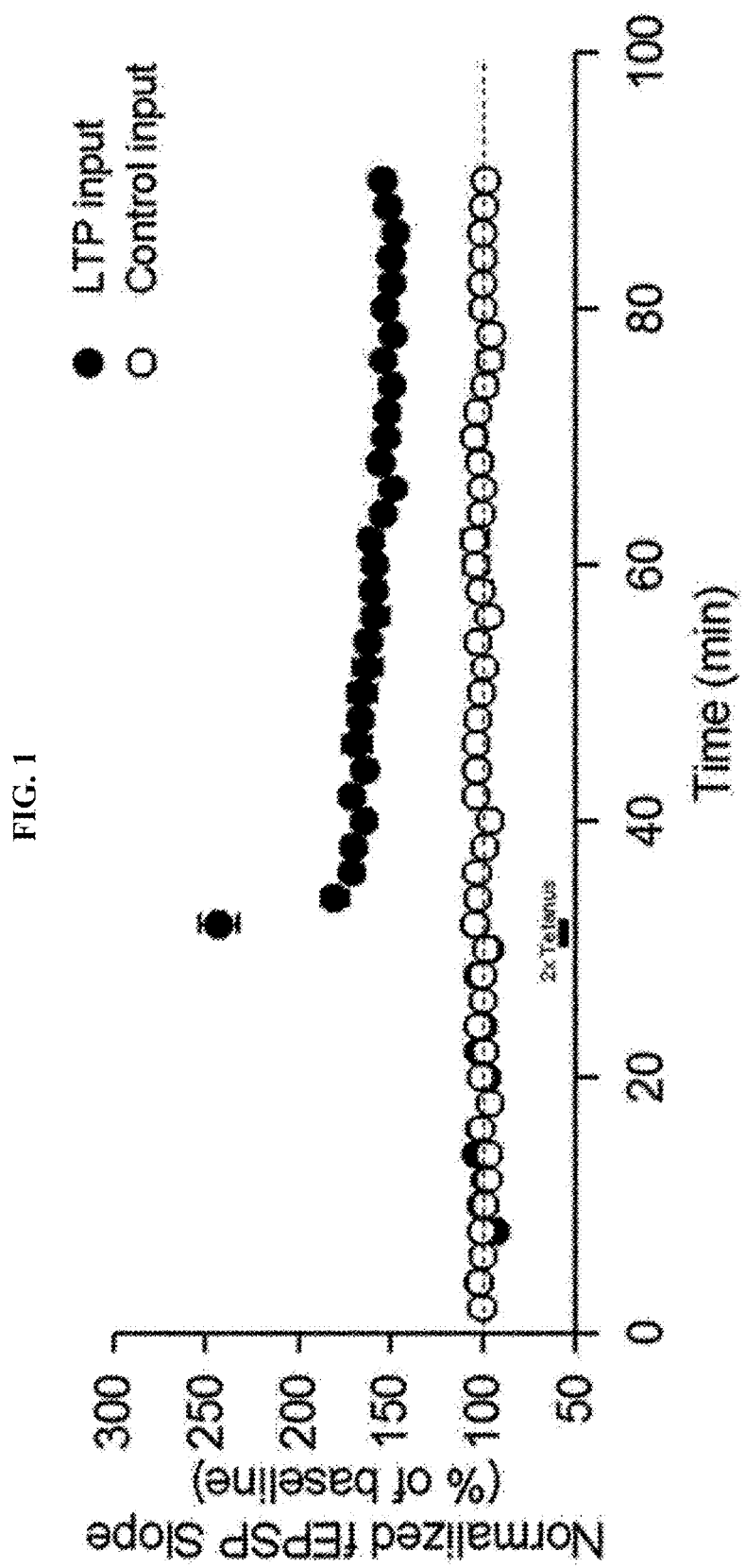
FIG. 1 is a graph showing results of an LTP induction experiment using a hippocampal slice of a normal mouse not treated with amyloid-β and avenanthramide C according to Experimental Example 1.
Figure 2:
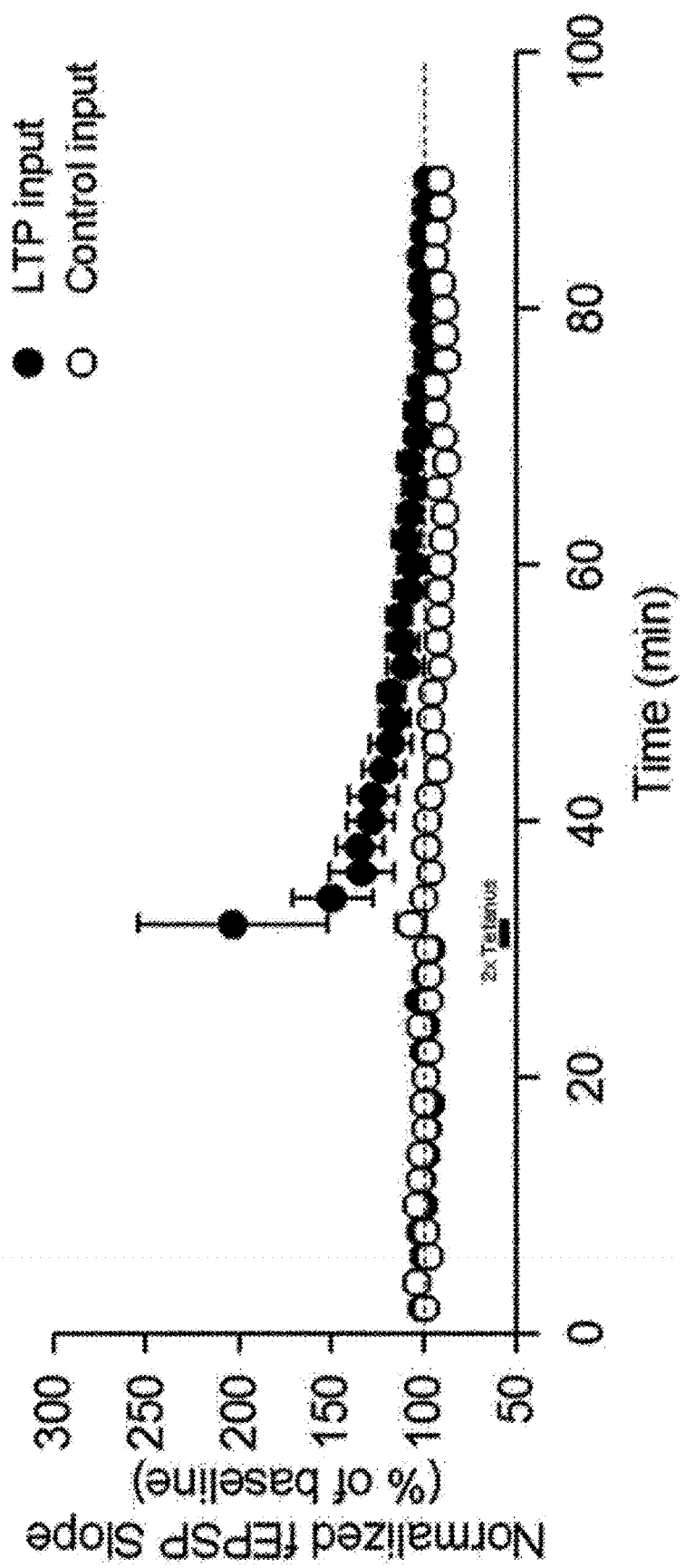
FIG. 2 is a graph showing results of an LTP induction experiment using a hippocampal slice of a mouse treated with 500 nM of amyloid-β according to Experimental Example 1.
Figure 3:
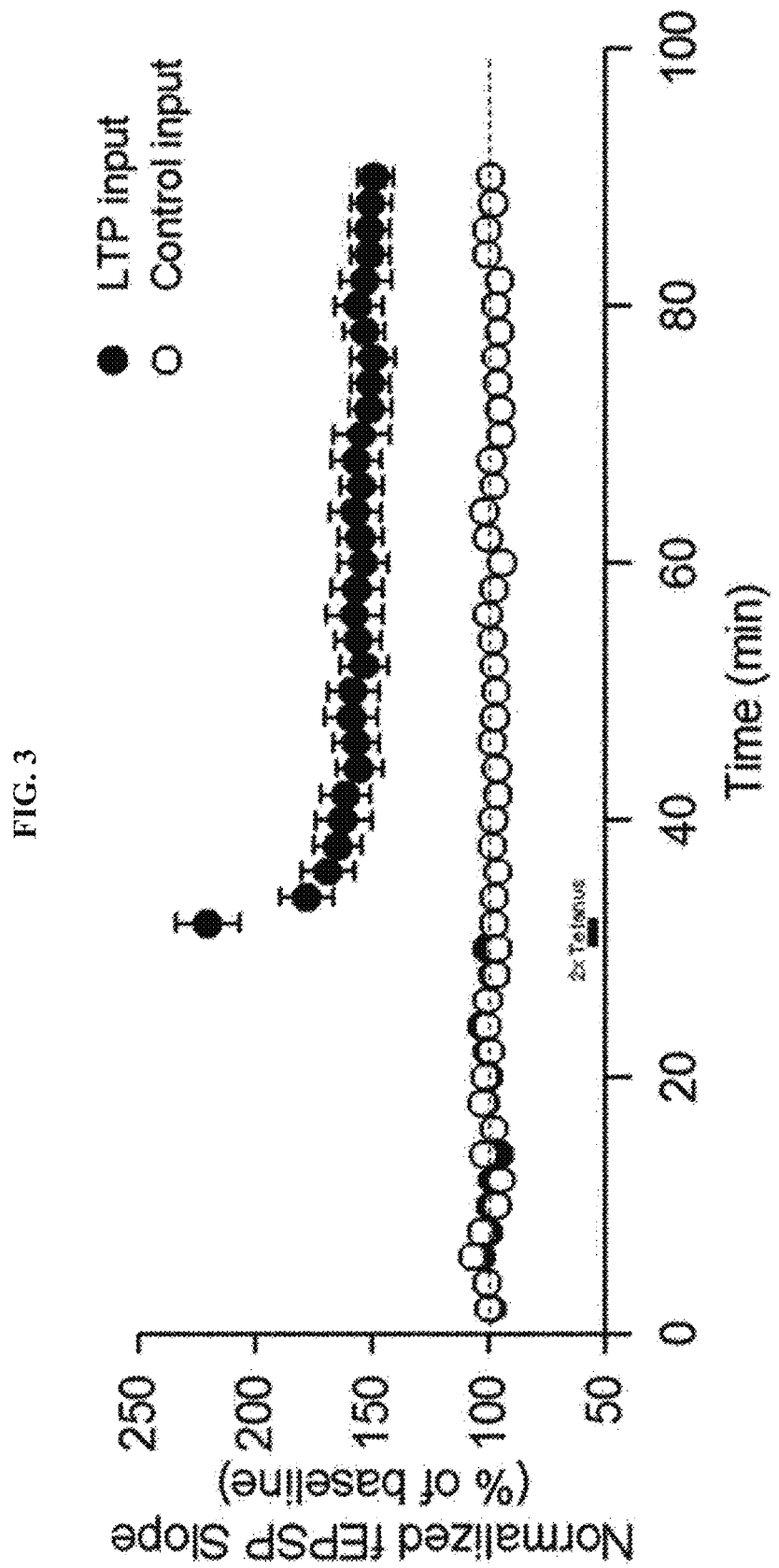
FIG. 3 is a graph showing results of an LTP induction experiment using a hippocampal slice of a mouse treated with 500 nM of amyloid-β and 50 μM of avenanthramide C according to Experimental Example 1.
Figure 4:
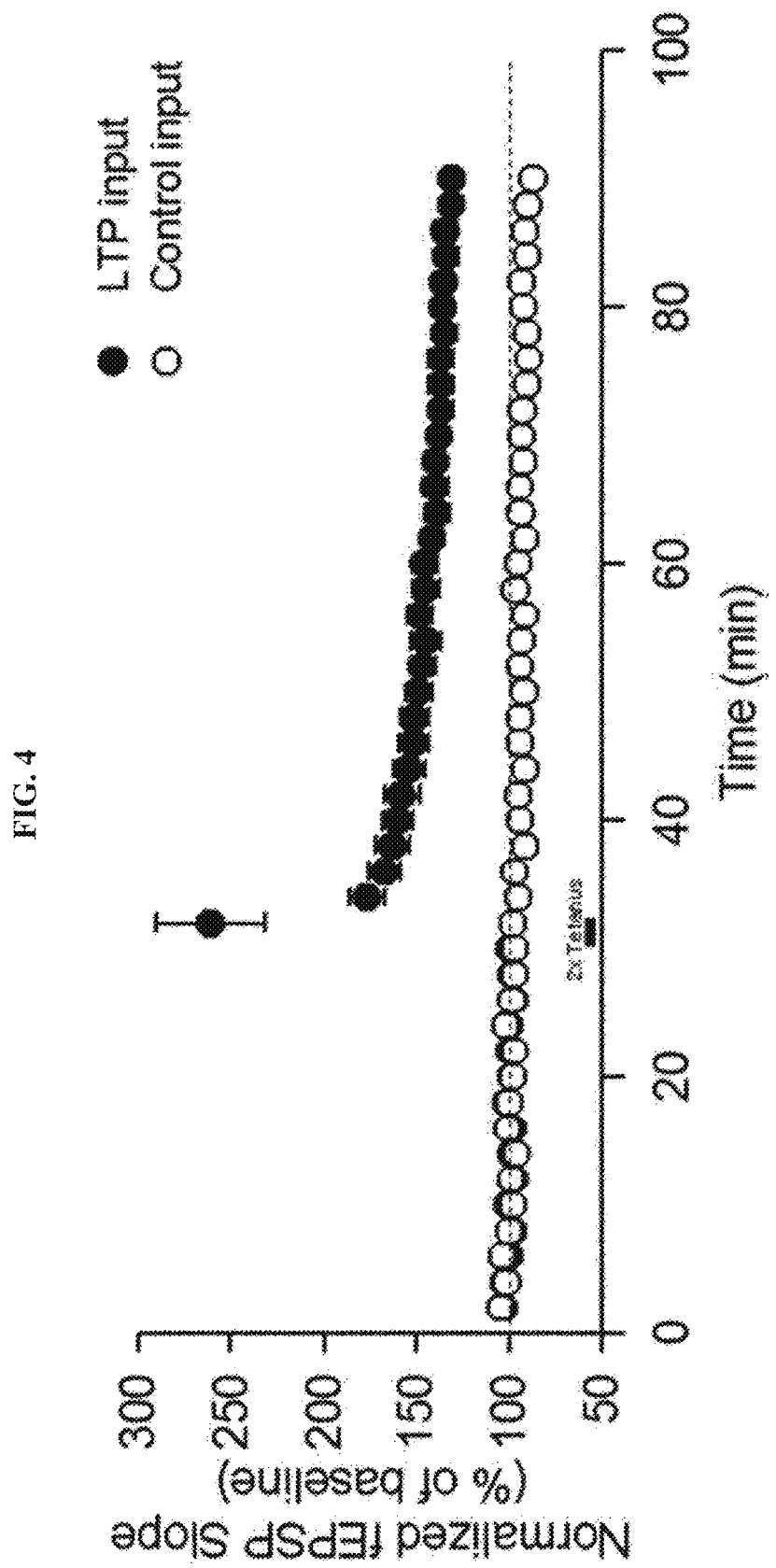
FIG. 4 is a graph showing results of an LTP induction experiment using a hippocampal slice of a mouse treated with only 50 μM of avenanthramide C according to Experimental Example 1.
Figure 5:
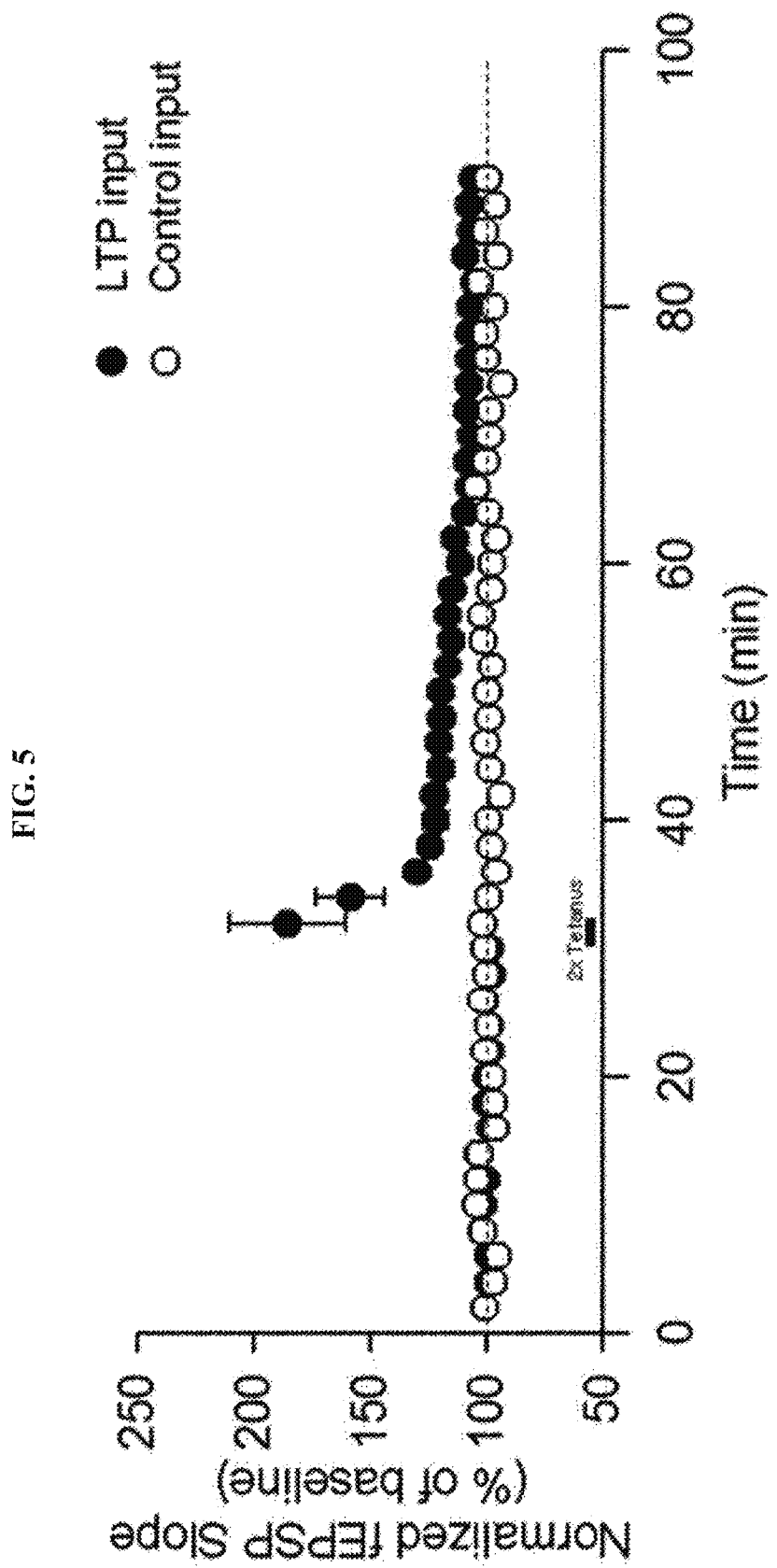
FIG. 5 is a graph showing results of an LTP induction experiment using a hippocampal slice of a mouse treated with 500 nM of amyloid-β and 10 μM of avenanthramide C according to Experimental Example 1.

As a result, LTP was induced in Sample 1 not treated with amyloid-β and avenanthramide C (FIG. 1), but the LTP was not induced in Sample 2 treated with 500 nM amyloid-β (FIG. 2). The LTP was induced in Sample 3 treated with 500 nM of amyloid-β and 50 μM of avenanthramide C together (FIG. 3). In addition, LTP was induced in Sample 4 treated with only 50 μM of avenanthramide C, similarly to Sample 1 (FIG. 4). Meanwhile, the LTP was not induced in Sample 5 treated with 500 nM of amyloid-β and 10 μM of avenanthramide C together (FIG. 5). That is, it was confirmed that, when providing the amyloid-β and the avenanthramide C together for treating the sample, supplying 10 μM of avenanthramide C did not prevent amyloid-β inhibiting LTP, but supplying 50 μM of avenanthramide C did prevent amyloid-β inhibiting LTP.

Figure 6:
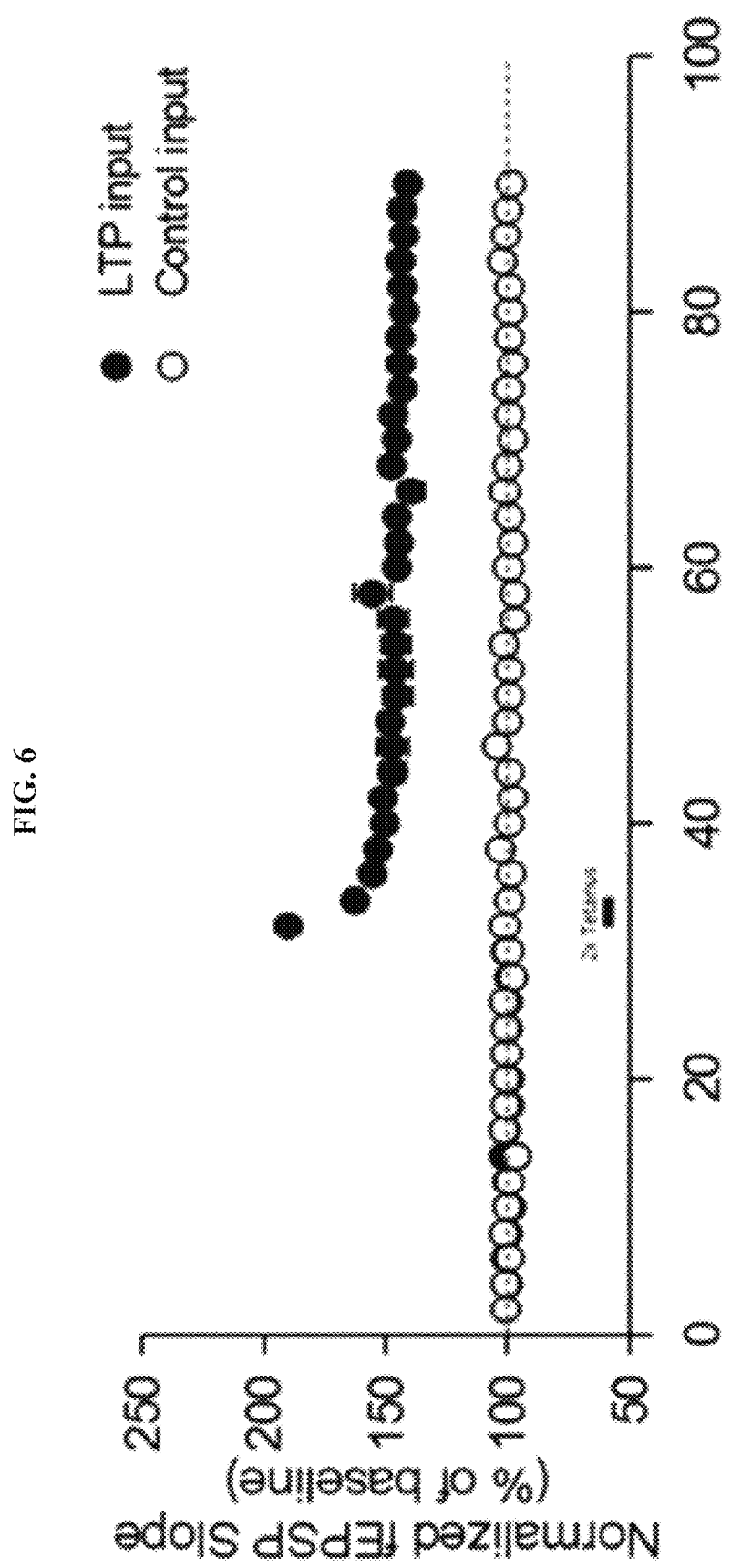
FIG. 6 is a graph showing results of an LTP induction experiment using a hippocampal slice of a mouse treated with only 500 μM of avenanthramide C according to Experimental Example 1.
Figure 7:
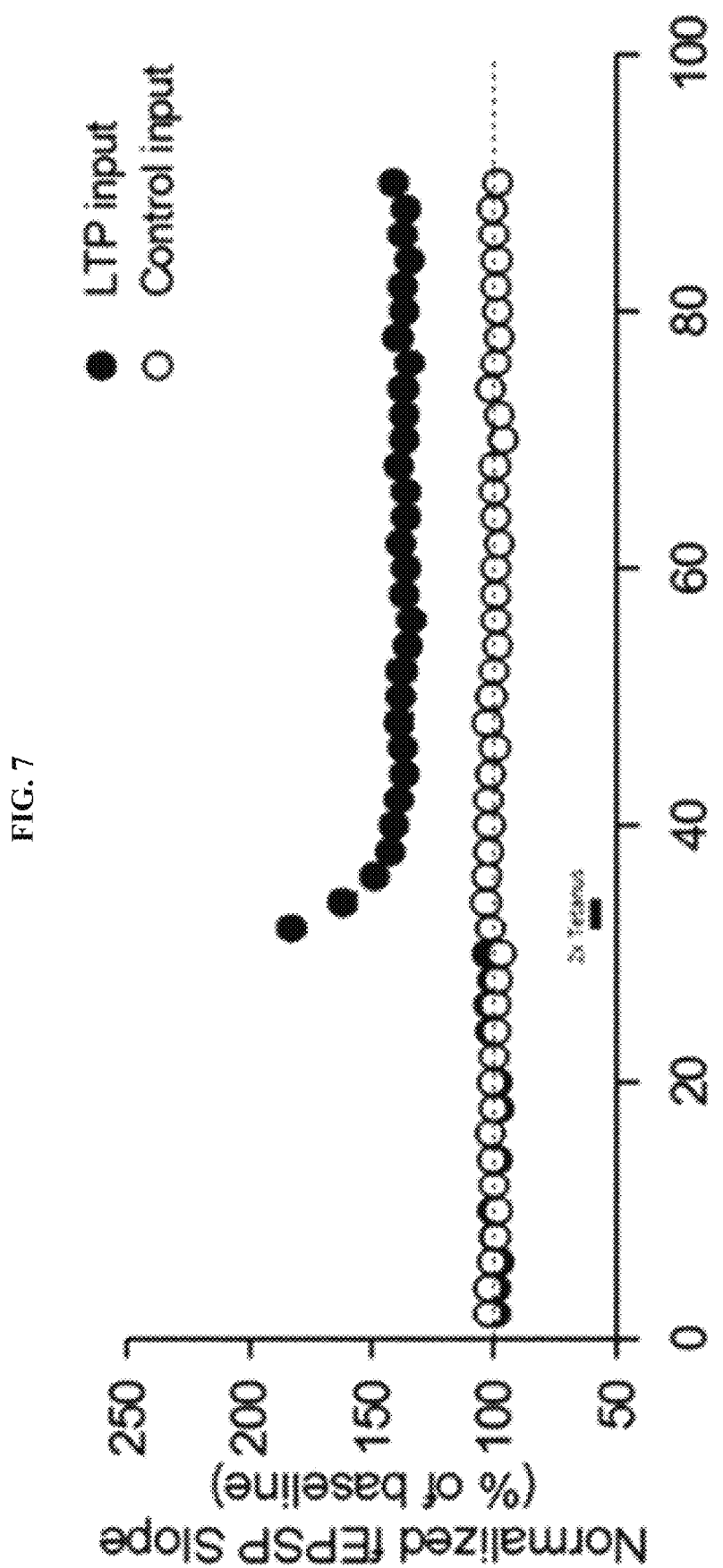
FIG. 7 is a graph showing results of an LTP induction experiment using a hippocampal slice of a mouse treated with 500 nM of amyloid-β and 500 μM of avenanthramide C according to Experimental Example 1.

Meanwhile, LTP was induced in Sample 5 treated with only 500 μM of avenanthramide C while not exhibiting toxicity, similarly to Sample 1 (FIG. 6). In addition, the LTP was also induced in Sample 6 treated with 500 nM of amyloid-β and 500 μM of avenanthramide C together (FIG. 7).

Figure 8:
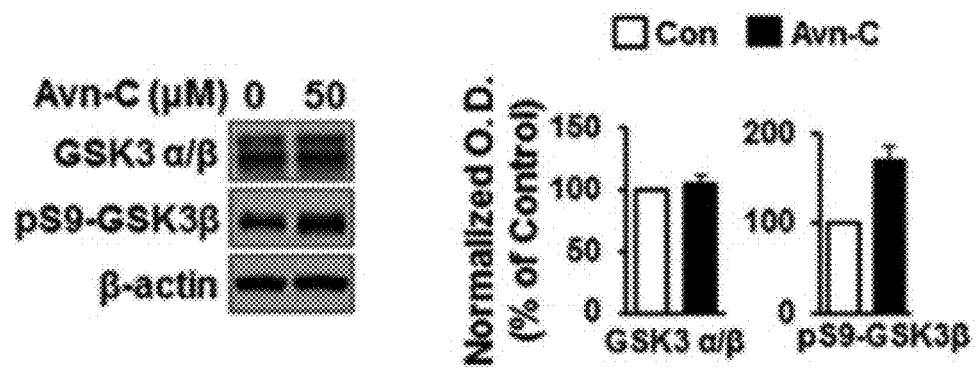
FIG. 8 are diagrams showing results of GSK3β activity comparison when treating the hippocampal slice with 500 nM of amyloid-β and 50 μM of avenanthramide C according to Experimental Example 2.
Figure 9:
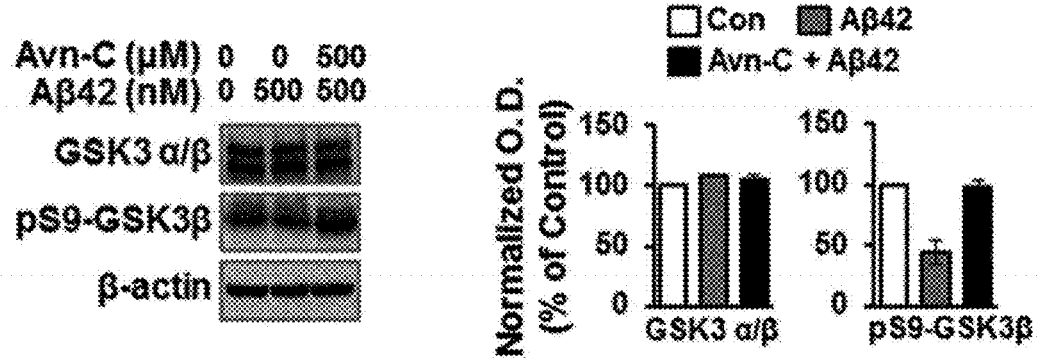
FIG. 9 are diagrams showing results of GSK3β activity comparison when treating the hippocampal slice with 500 nM of amyloid-β and 500 μM of avenanthramide C according to Experimental Example 2.

Experimental Example 2: Comparison of Activity of GSK3β Depending on Treatment with Avenanthramide C According to the Present Invention A hippocampal slice of a 4-month-old C57BL/6 mouse was treated with amyloid-β and avenanthramide C in amounts as illustrated in Table 1 above, and then was crushed on ice using a homogenizer after putting a radio-immunoprecipitation assay (RIPA) buffer into a tissue. Thereafter, RIPA [50 mM Tris-HCl (PH 7.5), 150 mM NaCl, 1% Nonidet P-40, 0.5% sodium deoxycholate, 0.1% SDS, 1 mM phenylmethylsulfonyl fluoride (PMSF), 1 mM DTT, and 2 μg of leupeptin and aprotinin, respectively, were dissolved therein. The crushed cells were centrifuged with 12,000 g at 4° C. for 20 minutes, and the resulting soluble fractions were denatured in a Laemmli buffer and subjected to sodium dodecyl sulfate-polyacrylamide gel electrophoresis (SDS-PAGE). After gel electrophoresis, the separated proteins were transferred to a polyvinylidene difluoride (PVDF) membrane using electroblotting. The membrane was blocked with AMRESCO, RAPIDBLOCK solution (pH 7) and subjected to blotting by using enhanced chemiluminescence (ECL). For blotting, an antibody for GSK3αβ and an antibody for phosphorylated GSK3β (S9) were used. The obtained results are illustrated in FIGS. 8 and 9. GSK3β is an enzyme whose activity is inhibited by the phosphorylation of serine residue 9, and is known as a modulator of a wide range of functions such as energy metabolism, cell proliferation, apoptosis and the like.

As a result, GSK3β was activated by treatment of amyloid-β, and when treating the sample with 500 nM of amyloid-β and 50 μM of avenanthramide C together, a result of inhibiting the activity of GSK3β was exhibited (FIG. 8). In addition, it was confirmed that activity of GSK3β was inhibited without toxicity even when treating the sample with 500 nM of amyloid-β and 500 μM of avenanthramide C together (FIG. 9).

Experimental Example 3: Effects of Avenanthramide C According to the Present Invention on Induced AD Mouse (Transgenic Mouse: 5×FAD Mouse)

Figure 10A:
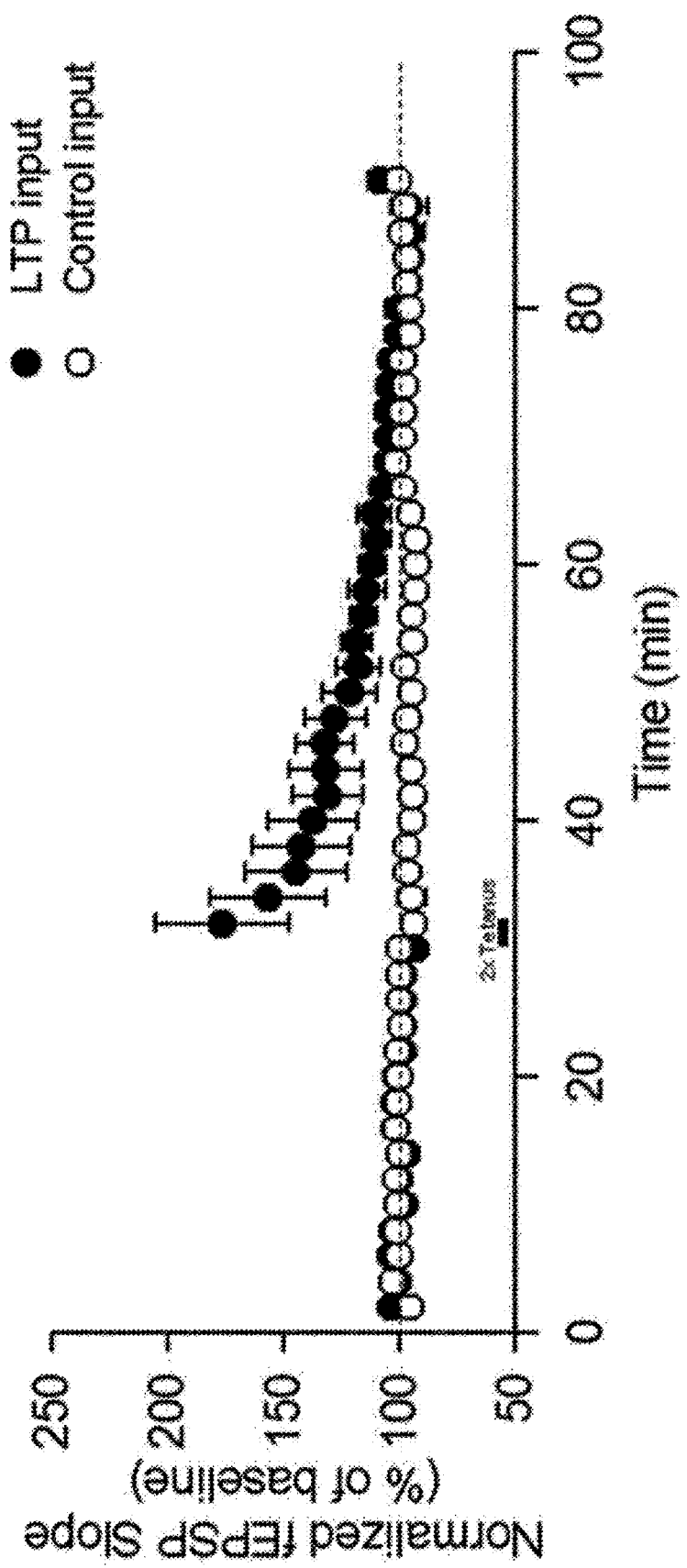
FIGS. 10A and 10B are graphs showing effects of avenanthramide C on the LTP in an induced Alzheimer's disease mouse ('induced AD mouse') according to Experimental Example 3 (FIG. 10A: avenanthramide C-untreated hippocampus slice, FIG. 10B: avenanthramide C-treated hippocampus slice).
Figure 10B:
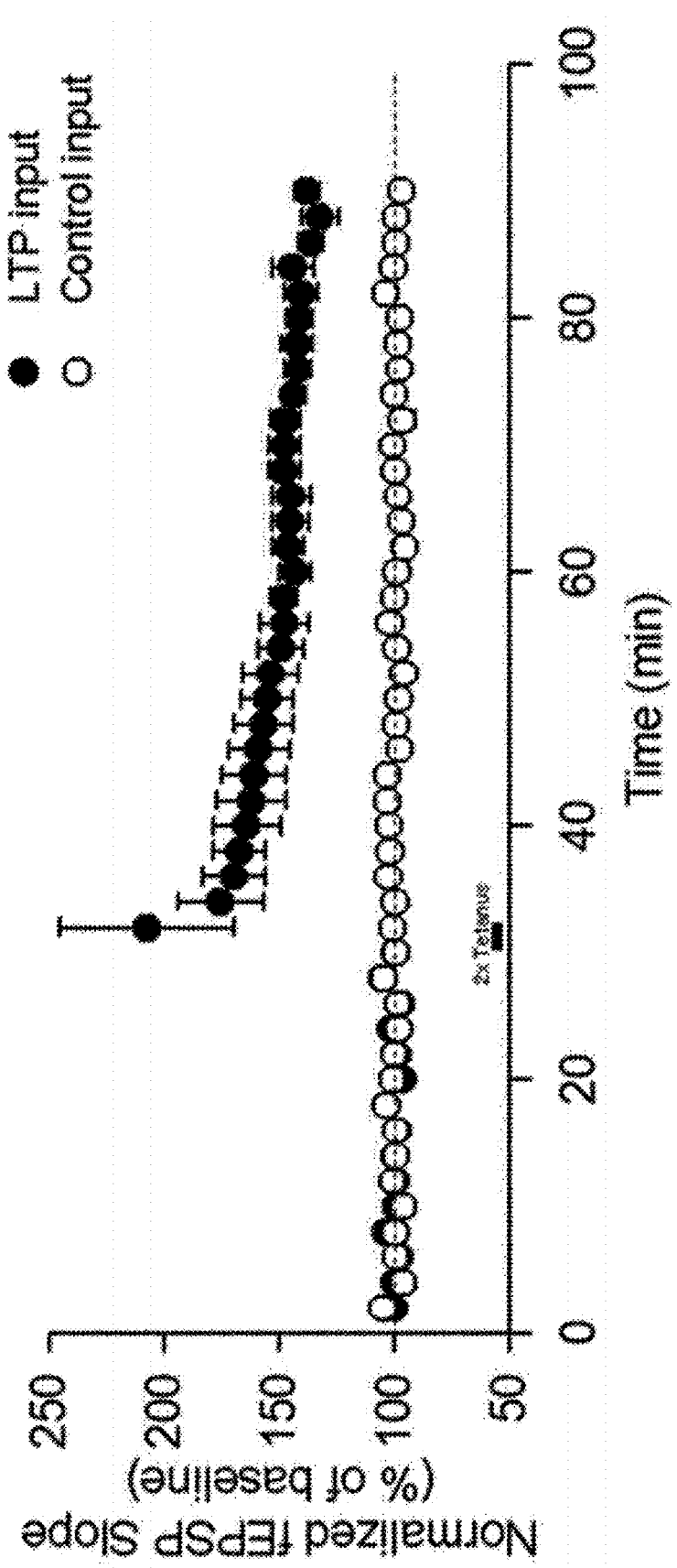

(1) Comparison of Long-Term Potentiation (LTP)
In order to examine effects of the avenanthramide C according to the present invention on the long-term potentiation in a hippocampal slice of a 4-month-old 5×FAD induced AD mouse, an LTP comparison experiment was performed using a hippocampal slice of a gene manipulated mouse in the same method as Experimental Example 1, and the results thereof are illustrated in FIGS. 10A and 10B.

As a result, it was confirmed that, the induced AD mouse failed to form the LTP (FIG. 10A), but the LTP was induced when treating the sample with 50 μM of avenanthramide C (FIG. 10B).
(2) Comparison of GSK3β Activity
In order to examine effects of avenanthramide C according to the present invention on activity of GSK3β in a hippocampal slice of a 4-month-old 5×FAD induced AD mouse, the same western blotting as Experimental Example 2 was performed using a hippocampal slice of a gene manipulated mouse, and the results thereof are illustrated in FIG. 11.

Figure 11:
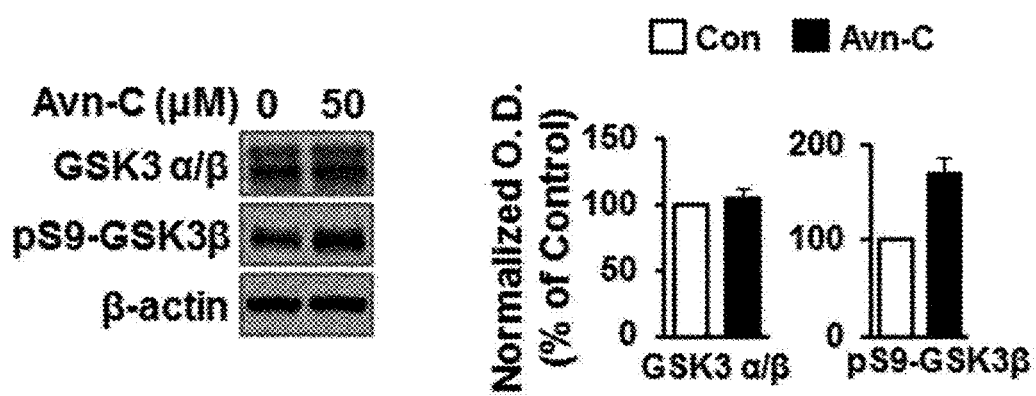
FIG. 11 is diagrams showing results of western blotting according to Experimental Example 3.

As a result, it was confirmed that the activity of GSK3β in a case of treating the sample with 50 μM of avenanthramide C was more inhibited than a case of not treating the sample with avenanthramide C (FIG. 11).

Experimental Example 4: Effects of Avenanthramide C According to the Present Invention on Another Induced AD Mouse (Transgenic Mouse: Tg2576 Mouse)

Figure 12A:
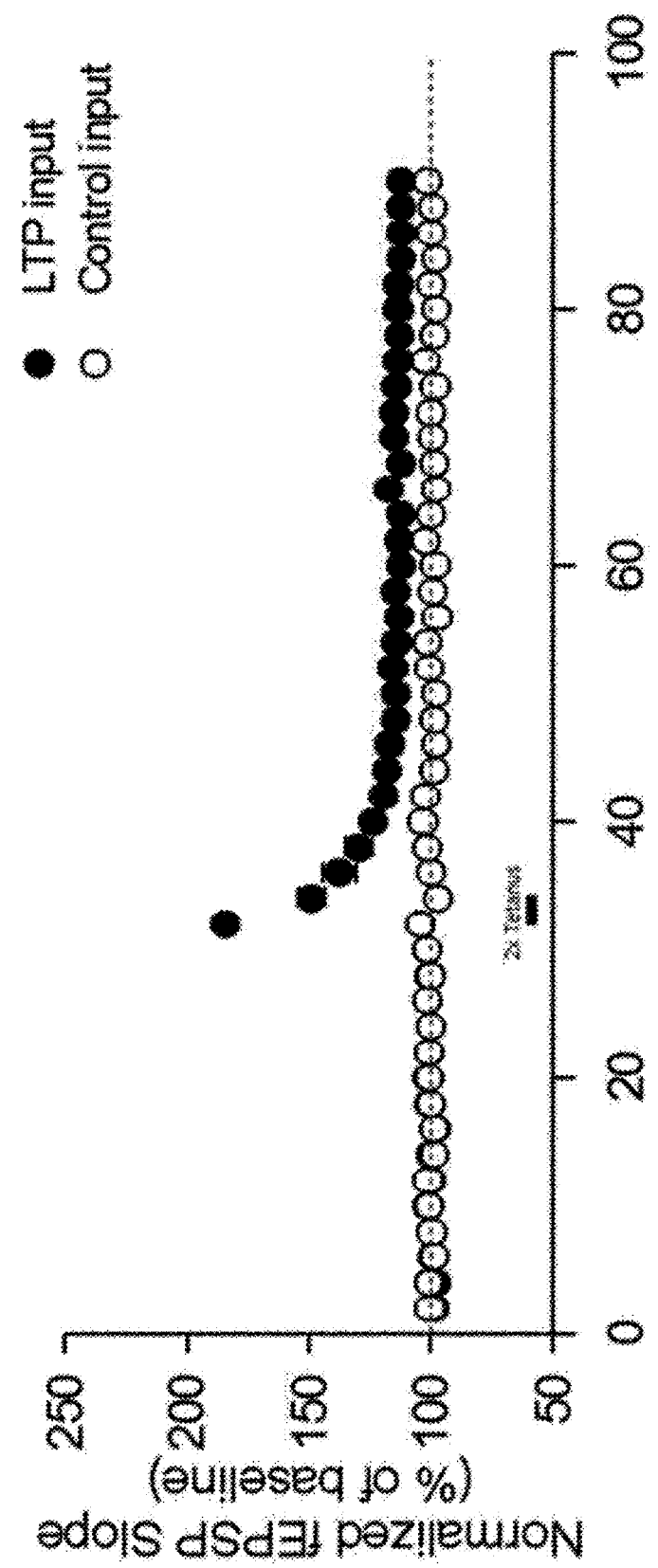
FIGS. 12A and 12B are graphs showing effects of avenanthramide C on LTP in an induced AD mouse according to Experimental Example 4.
Figure 12B:
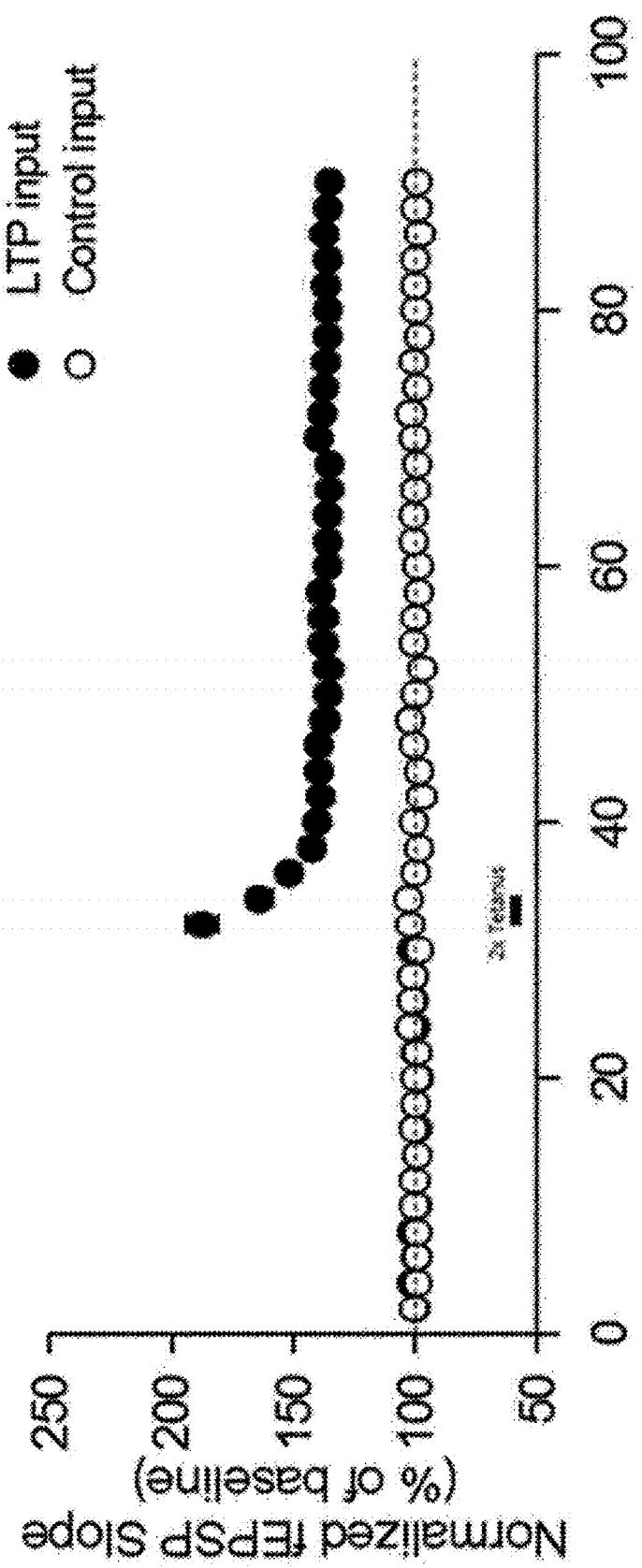

(1) Comparison of Long-Term Potentiation (LTP)
In order to examine effects of avenanthramide C according to the present invention on the LTD in a hippocampal slice of a 7-month-old Tg2576 induced AD mouse, an LTP comparison experiment was performed using a hippocampal slice of a gene manipulated mouse in the same method as Experimental Example 1, and the results thereof are illustrated in FIGS. 12A and 12B.

As a result, it was confirmed that, the induced AD mouse failed to form the LTP (FIG. 12A), but the LTP was induced when treating the sample with 50 μM of avenanthramide C (FIG. 12B).
(2) Comparison of GSK3β Activity
In order to examine effects of avenanthramide C according to the present invention on activity of GSK3β in a hippocampal slice of a 7-month-old Tg2576 induced AD mouse, the same western blotting as Experimental Example 2 was performed using a hippocampal slice of a gene manipulated mouse, and the results thereof are illustrated in FIG. 13.

Figure 13:
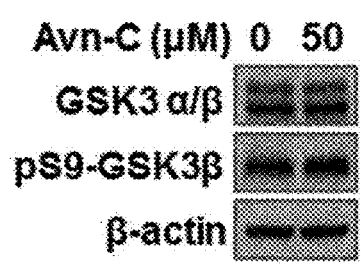
FIG. 13 is a diagram showing the results of western blotting according to Experimental Example 4.
Figure 13:
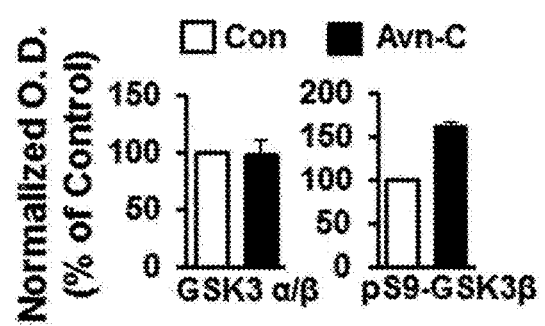

As a result, it was confirmed that the activity of GSK3β in a case of treating the sample with 50 μM of avenanthramide C was more inhibited than a case of not treating the sample with avenanthramide C (FIG. 13).

Figure 14A:
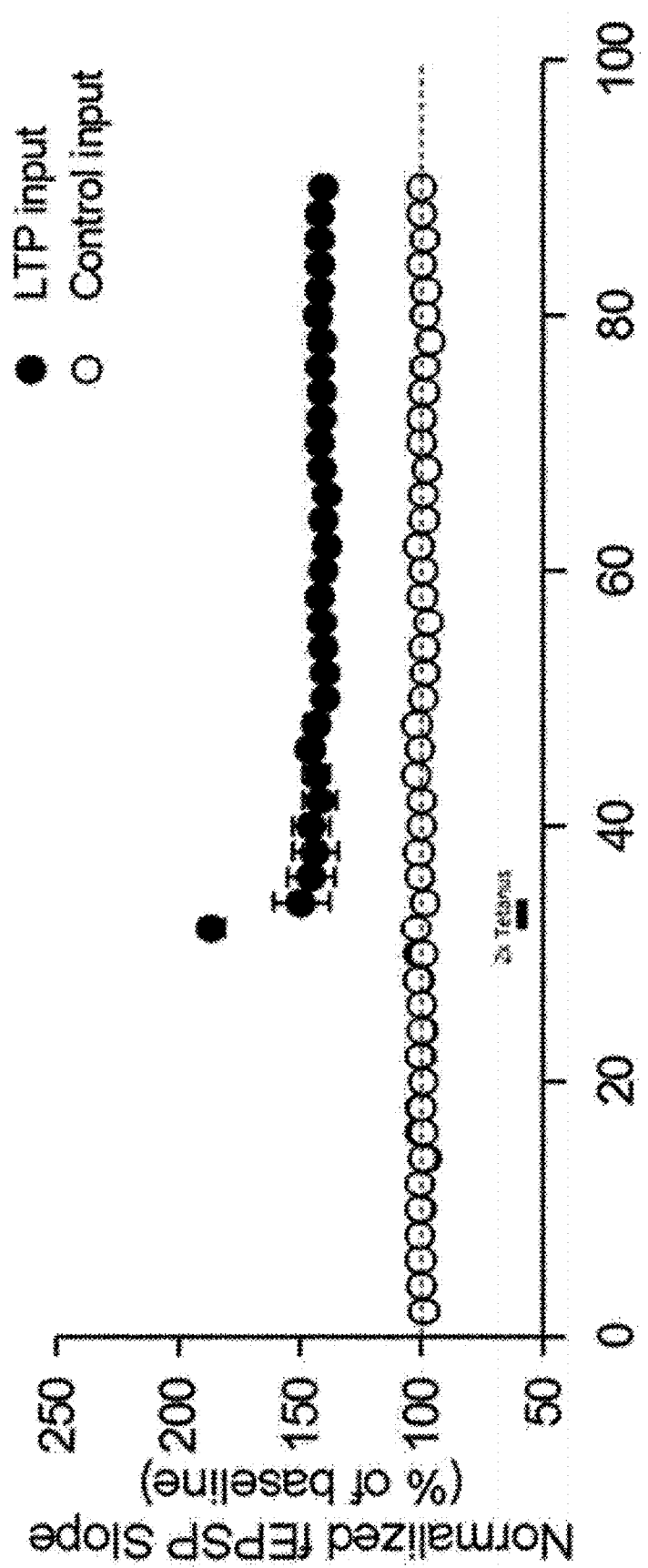
FIGS. 14A to 14C are graphs showing effects of avenanthramide C methyl ester on the LTP in a mouse according to Experimental Example 5 (FIG. 14A: amyloid-β and avenanthramide C-untreated hippocampal slice, FIG. 14B: 500 nM amyloid-β-treated hippocampal slice, and FIG. 14C: 50 μM avenanthramide C methyl ester and 500 nM amyloid-β-treated hippocampal slice).
Figure 14B:
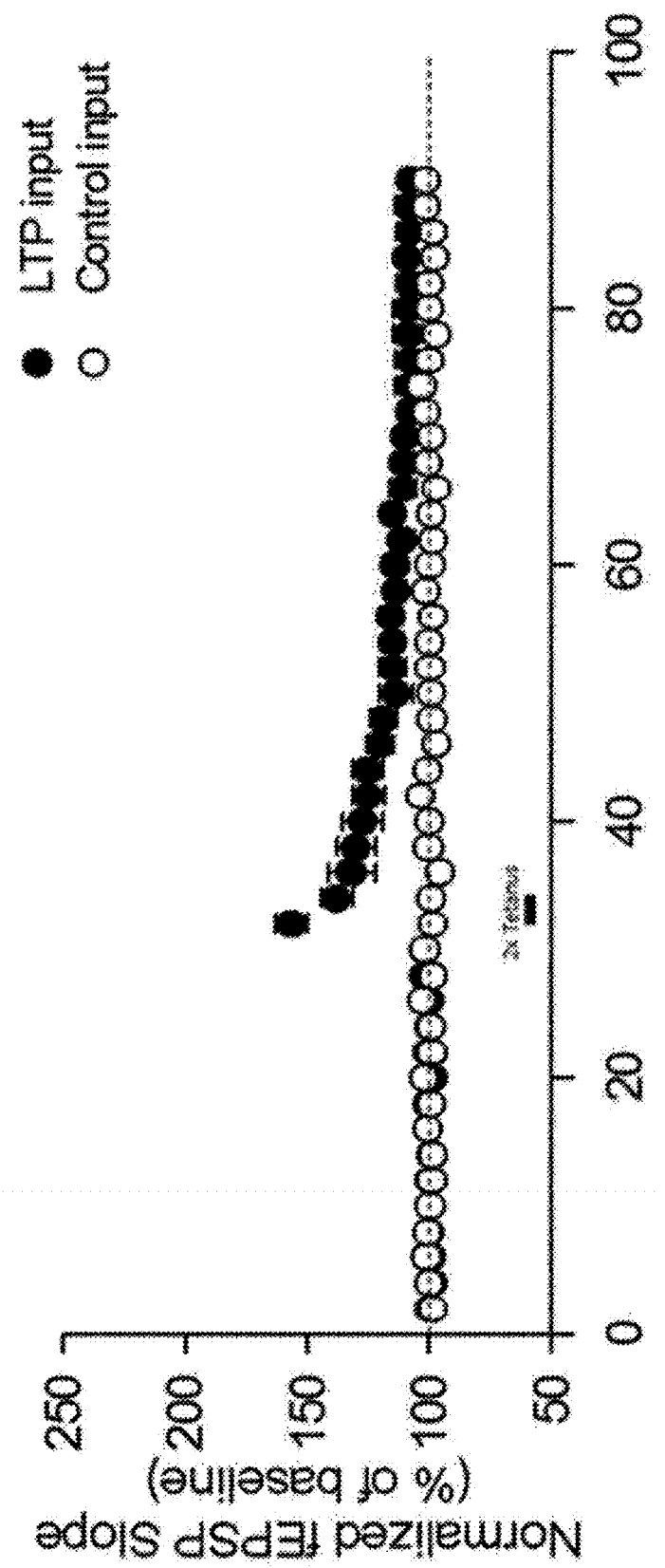

Experimental Example 5. Comparison of Long-Term Potentiation (LTP) and GSK3β Activity Depending on the Treatment of Avenanthramide C Methyl Ester According to the Present Invention (1) Comparison of Long-Term Potentiation (LTP)
In order to examine effects of avenanthramide C methyl ester according to the present invention on the LTD in a hippocampal slice of a mouse, an LTP comparison experiment was performed in the same method as Experimental Example 1, and the results thereof are illustrated in FIGS. 14A to 14C.

Figure 14C:
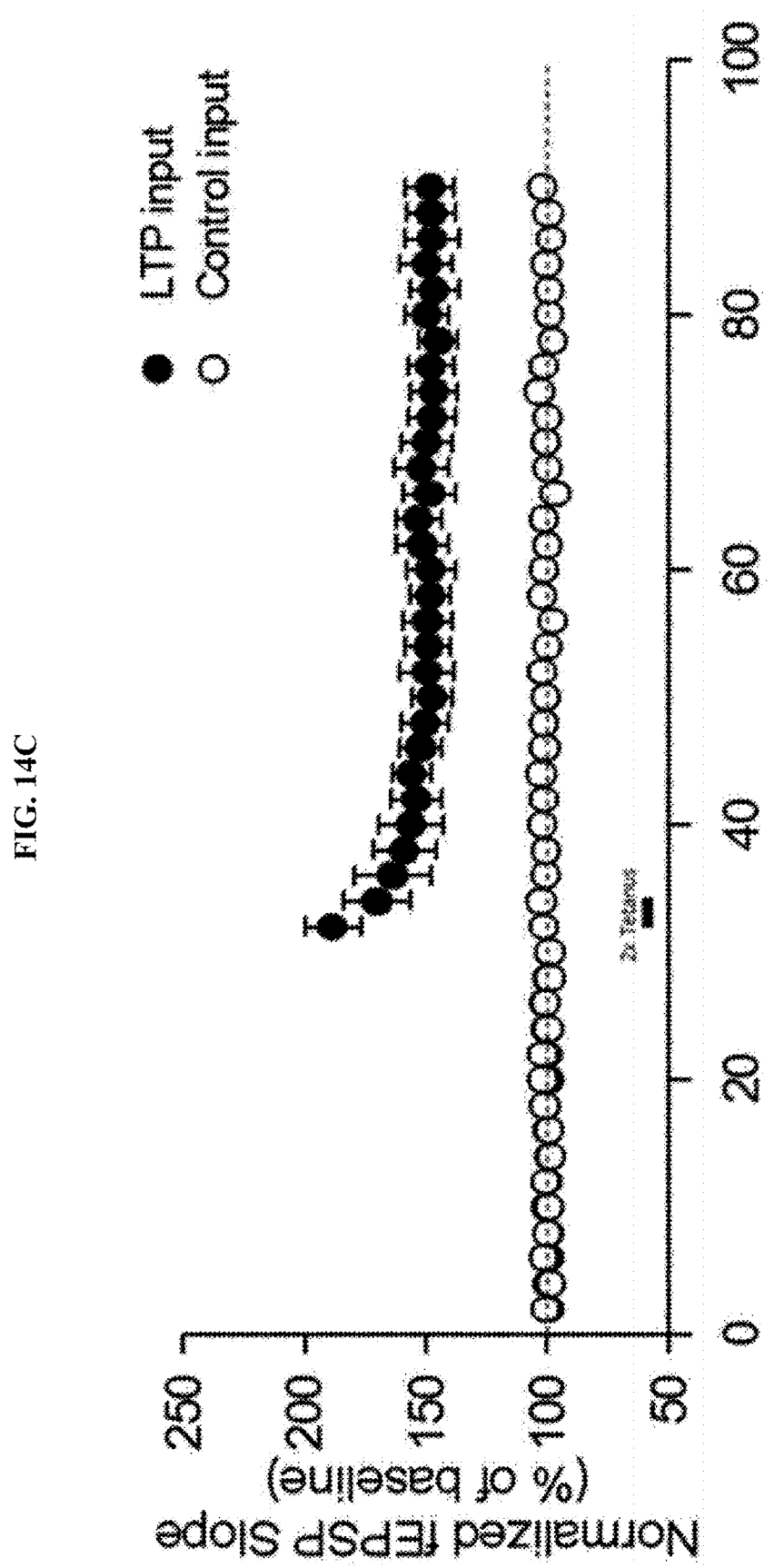

As a result, it was confirmed that, LTP was induced when not treating the sample with amyloid-β and avenanthramide C methyl ester (FIG. 14A), and the LTP was not induced when treating the sample with 500 nM amyloid-β (FIG. 14B), but the LTP was induced when treating the sample with 50 μM of avenanthramide C methyl ester and 500 nM of amyloid-β together (FIG. 14C).
(2) Comparison of GSK3β Activity
In order to examine effects of avenanthramide C methyl ester according to the present invention on activity of GSK3β in a hippocampal slice of a mouse, the same western blotting as Experimental Example 2 was performed, and the results thereof are illustrated in FIG. 15.

Figure 15:
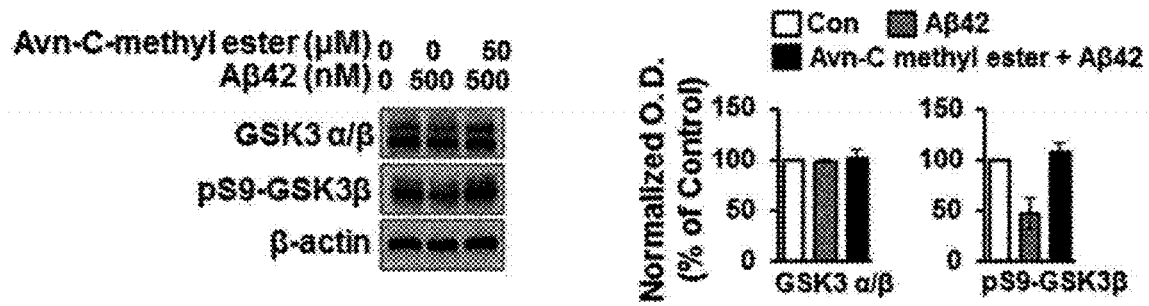
FIG. 15 is diagrams showing results of western blotting according to Experimental Example 5.

As a result, it was confirmed that the activity of GSK3β was inhibited when treating the sample with 50 μM of avenanthramide C methyl ester and 500 nM of amyloid-β together (FIG. 15).

Figure 16A:
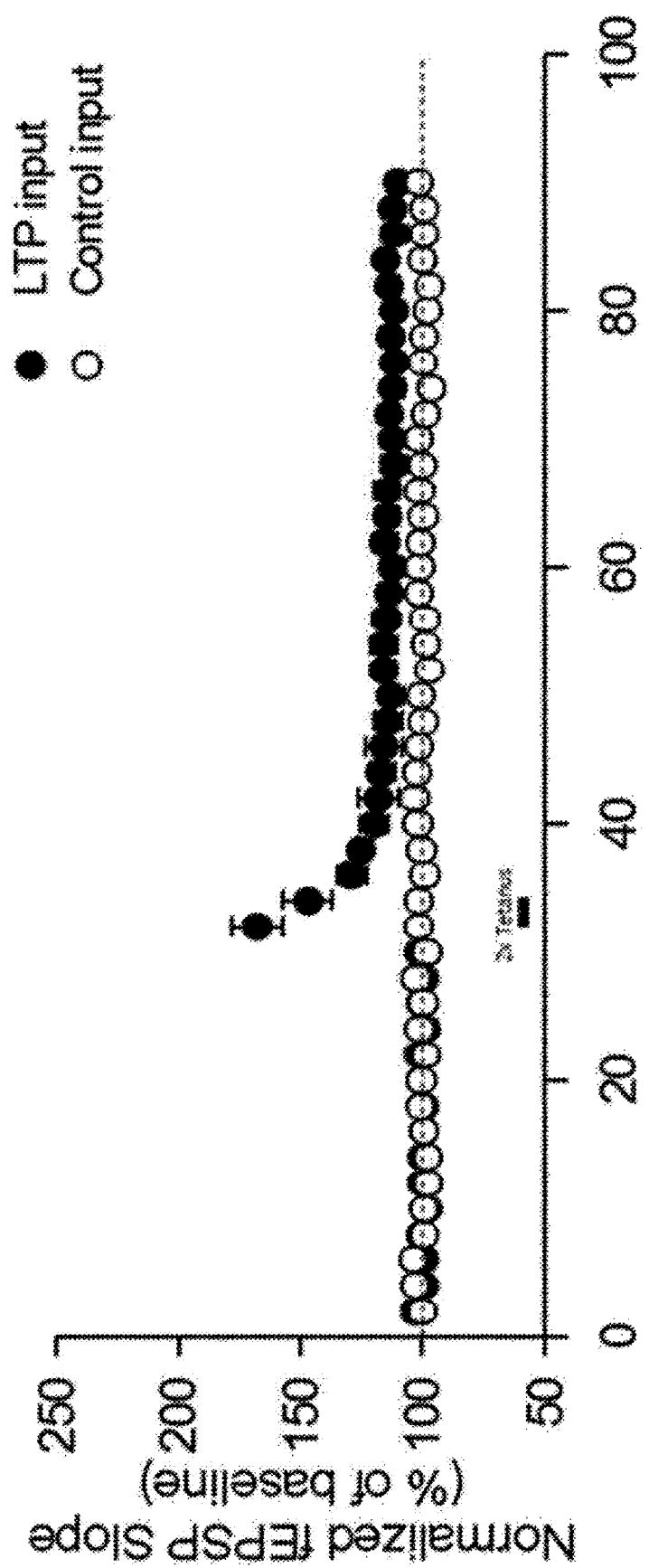
FIGS. 16A and 16B are graphs showing effects of avenanthramide B on the LTP in an induced AD mouse according to Experimental Example 6 (FIG. 16A: avenanthramide B-untreated hippocampal slice, and FIG. 16B: avenanthramide B-treated hippocampal slice).

Experimental Example 6: Effects of Avenanthramide B on Induced AD Mouse (Transgenic Mouse: Tg2576 Mouse) as a Comparative Example In order to examine effects of avenanthramide B methyl ester according to the present invention on the LTD in a hippocampal slice of a 7-month-old Tg2576 induced AD mouse, an LTP comparison experiment was performed in the same method as Experimental Example 1 using a hippocampal slice of a gene manipulated mouse, and the results thereof are illustrated in FIGS. 16A and 16B.

Figure 16B:
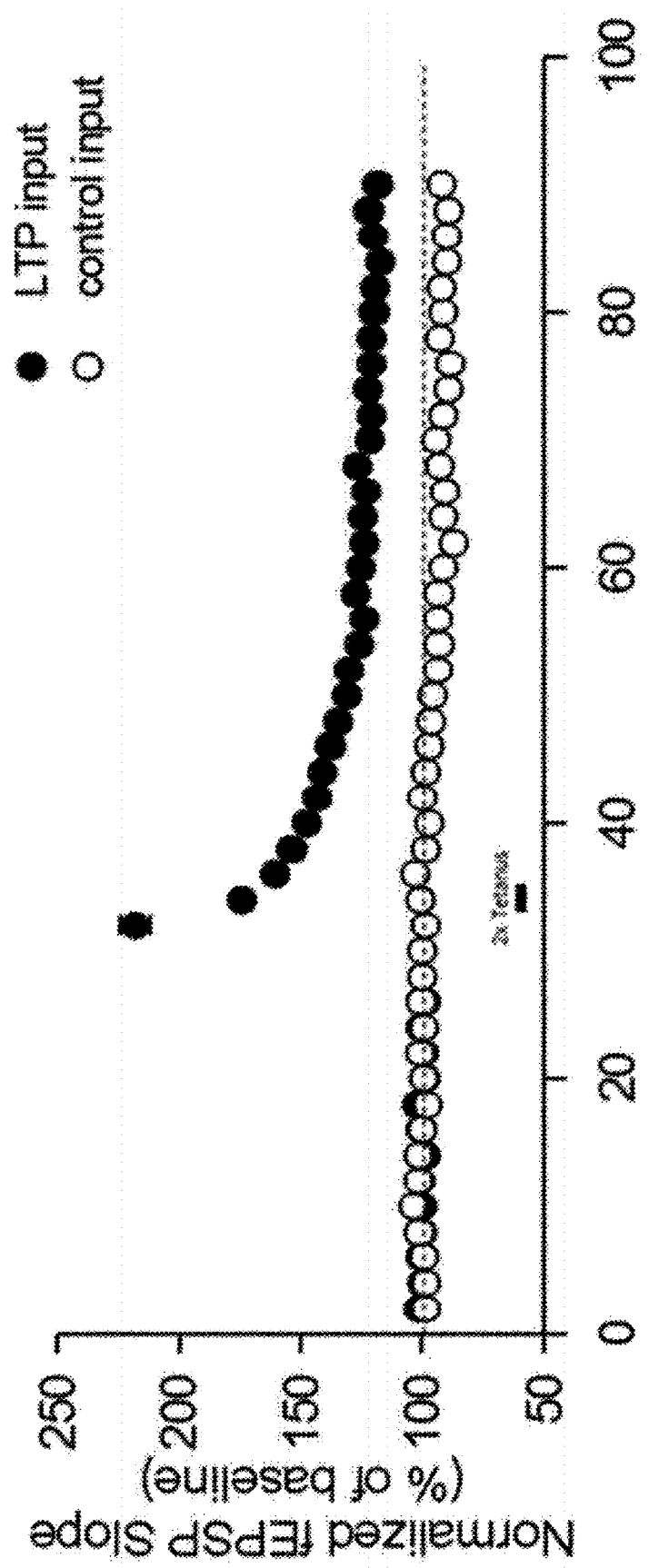

As a result, it was confirmed that the induced AD mouse failed to form the LTP (FIG. 16A), and the LTD was slightly induced when treating the sample with 50 μM of avenanthramide B, but it was not completely recovered, unlike the case of treating the sample with avenanthramide C (FIG. 16B).

Figure 17A:
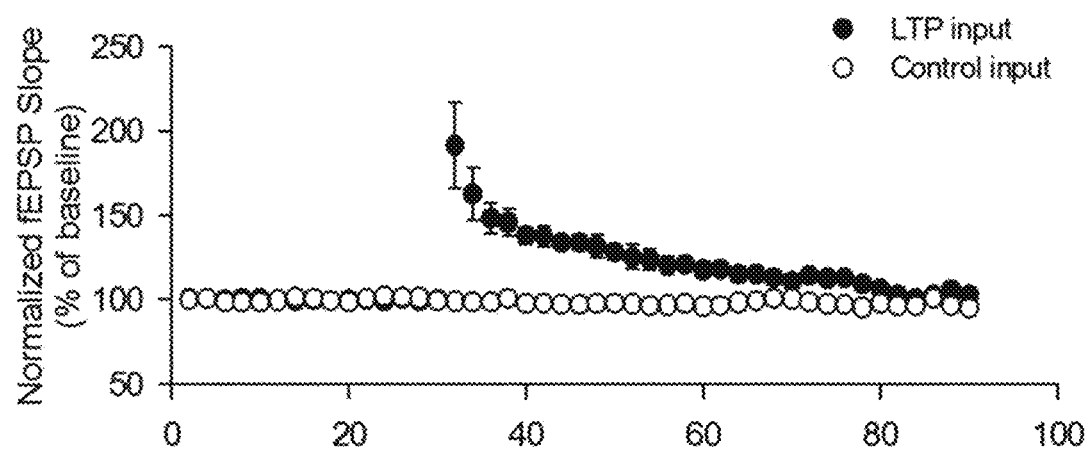
FIGS. 17A and 17B are graphs showing effects of avenanthramide A on the LTP in an induced AD mouse according to Experimental Example 7 (FIG. 17A: avenanthramide A-untreated hippocampal slice, and FIG. 17B: avenanthramide A-treated hippocampal slice).

Experimental Example 7: Effects of Avenanthramide a on Induced AD Mouse (Transgenic Mouse: Tg2576 Mouse) as a Comparative Example In order to examine effects of avenanthramide A according to the present invention on the LTD in a hippocampal slice of a 7-month-old Tg2576 induced AD mouse, an LTP comparison experiment was performed in the same method as Experimental Example 1 using a hippocampal slice of a gene manipulated mouse, and the results thereof are illustrated in FIGS. 17A and 17B.

Figure 17B:
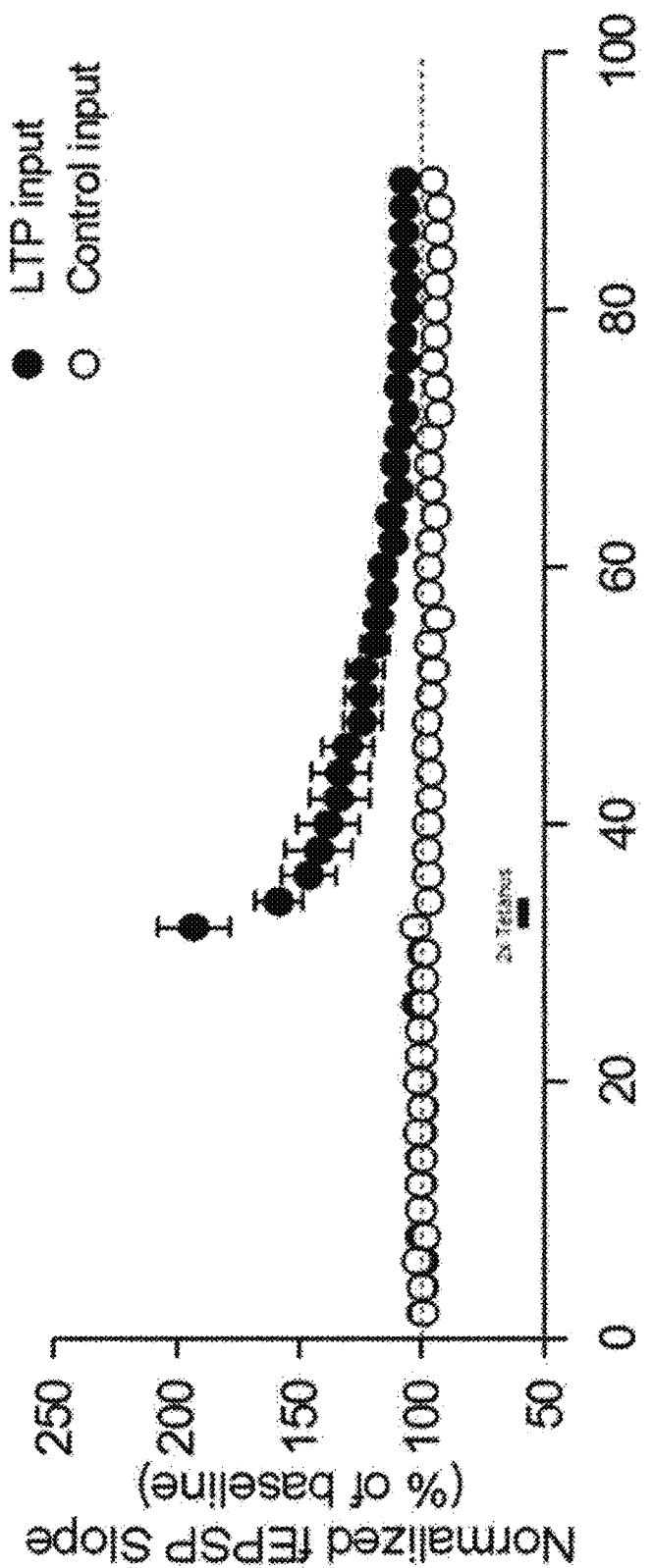
Figure 18:
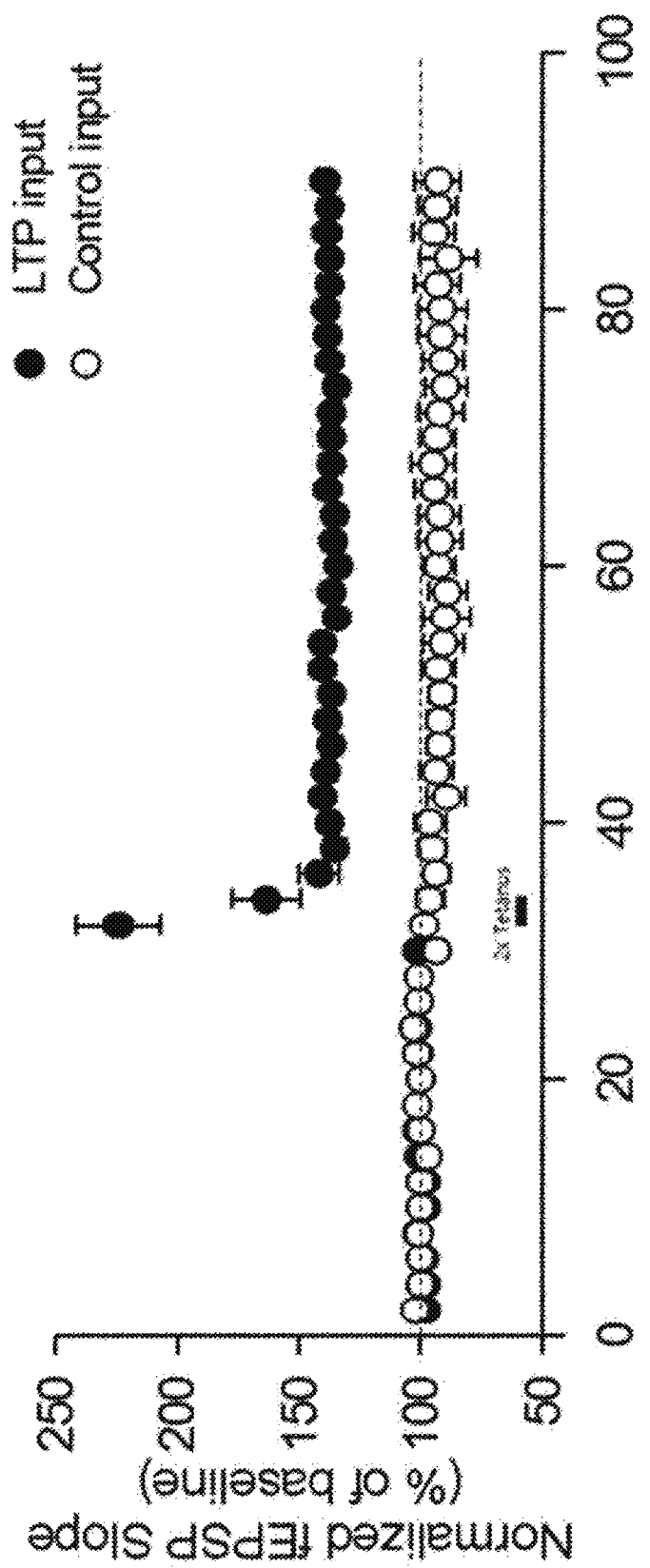
FIG. 18 is a graph showing results of an LTP induction experiment using a hippocampal slice of a normal mouse not treated with amyloid-β and β-glucan according to Experimental Example 8.

As a result, it was confirmed that, the induced AD mouse failed to form the LTP (FIG. 17A), but the LTP was induced when treating the sample with 50 μM of avenanthramide A (FIG. 17B).

Experimental Example 8. Comparison of Long-Term Potentiation (LTP) Depending on Treatment with Beta-Glucan (β-Glucan) as a Comparative Example An LTP comparison experiment was performed by treating the samples with amyloid-β and β-glucan in amounts as illustrated in Table 2 below two hours before the experiment by using the same method as in Experimental Example 1, except that β-glucan was used instead of avenanthramide C according to the present invention. The obtained results are illustrated in FIGS. 18 to 21.

TABLE 2

| No. | Amyloid-β | β-glucan |
| --- | --- | --- |
| Sample 6 | — | — |
| Sample 7 | 500 nM | — |
| Sample 8 | 500 nM | 80 μg/ml |
| Sample 9 | — | 50 μg/ml |

Figure 19:
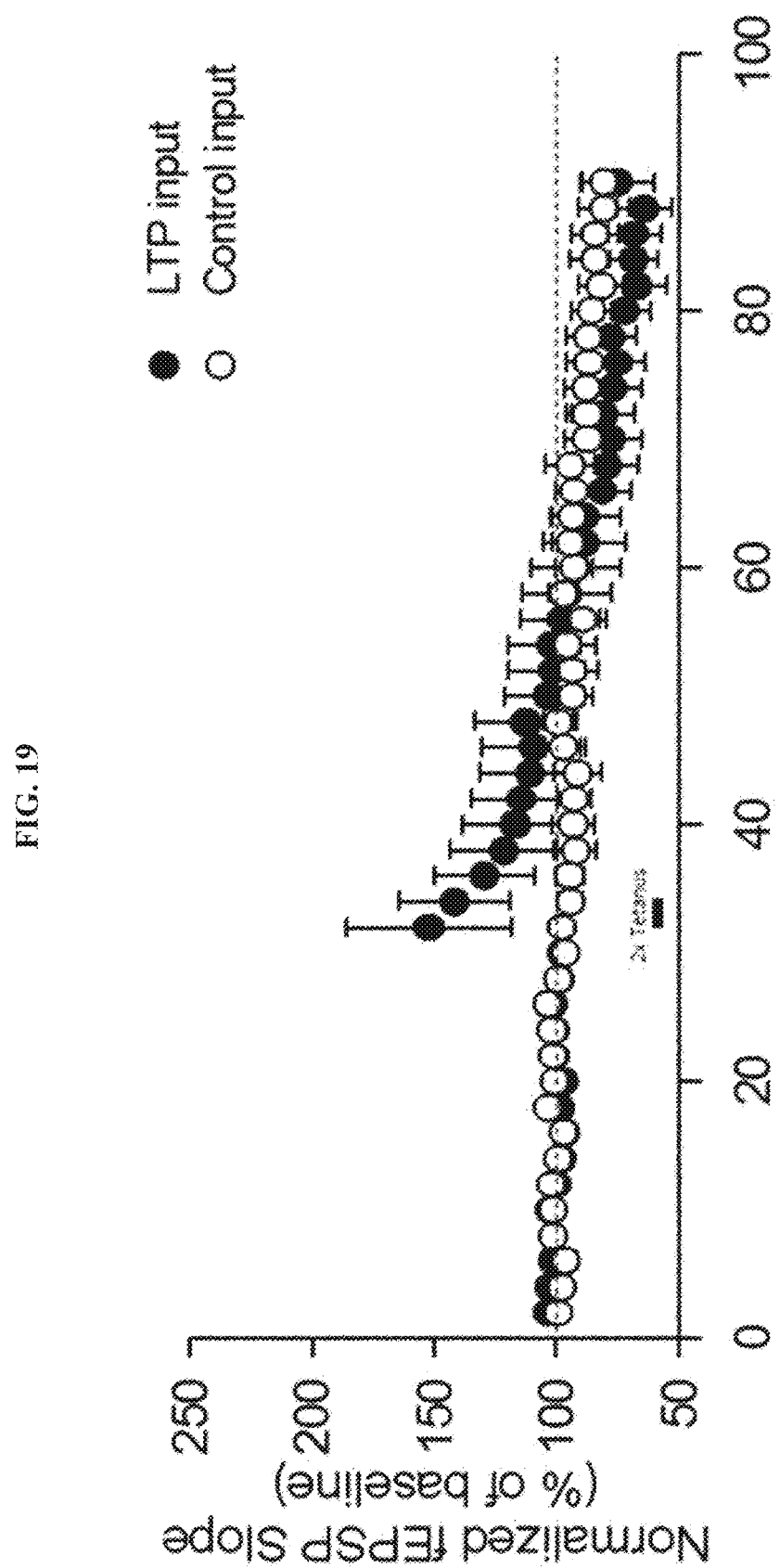
FIG. 19 is a graph showing results of an LTP induction experiment using a hippocampal slice of a mouse treated with 500 nM of amyloid-β according to Experimental Example 8.
Figure 20:
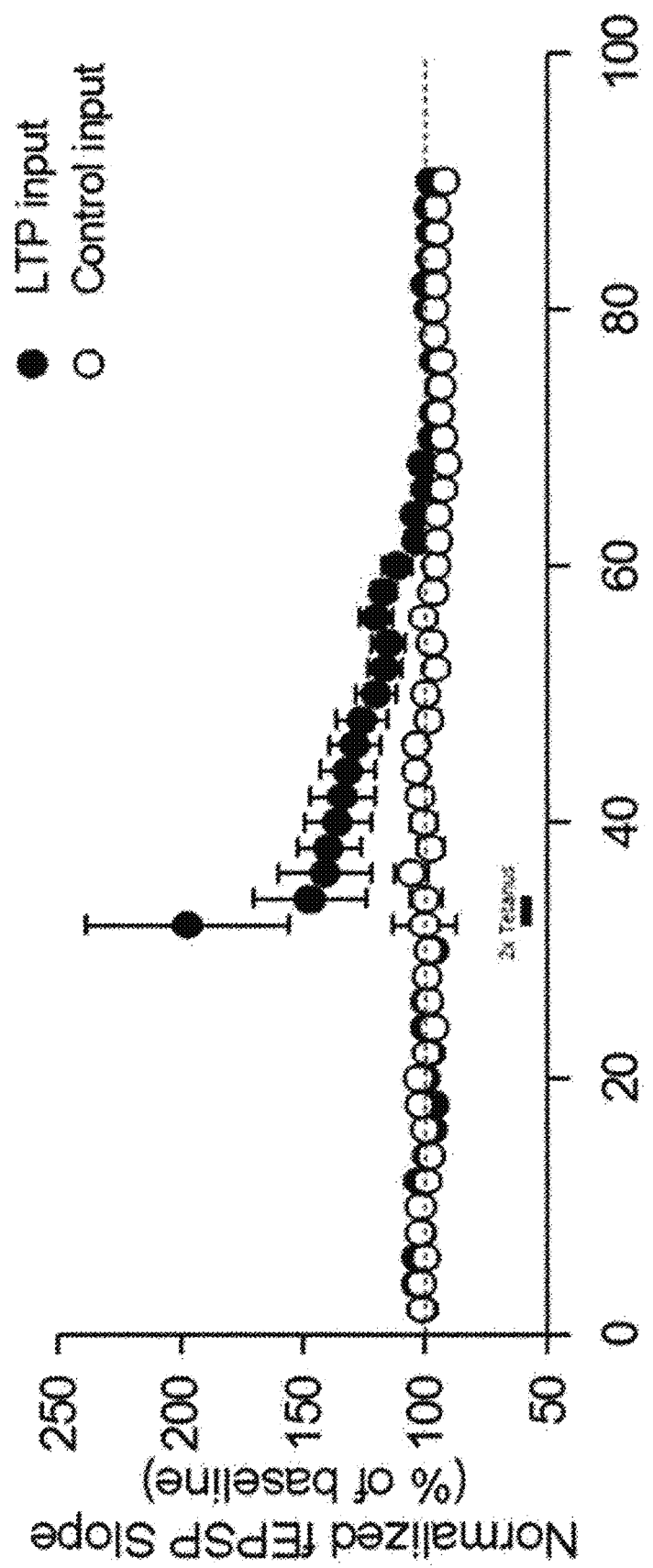
FIG. 20 is a graph showing results of an LTP induction experiment using a hippocampal slice of a mouse treated with 500 nM of amyloid-β and 80 nM of β-glucan according to Experimental Example 8.
Figure 21:
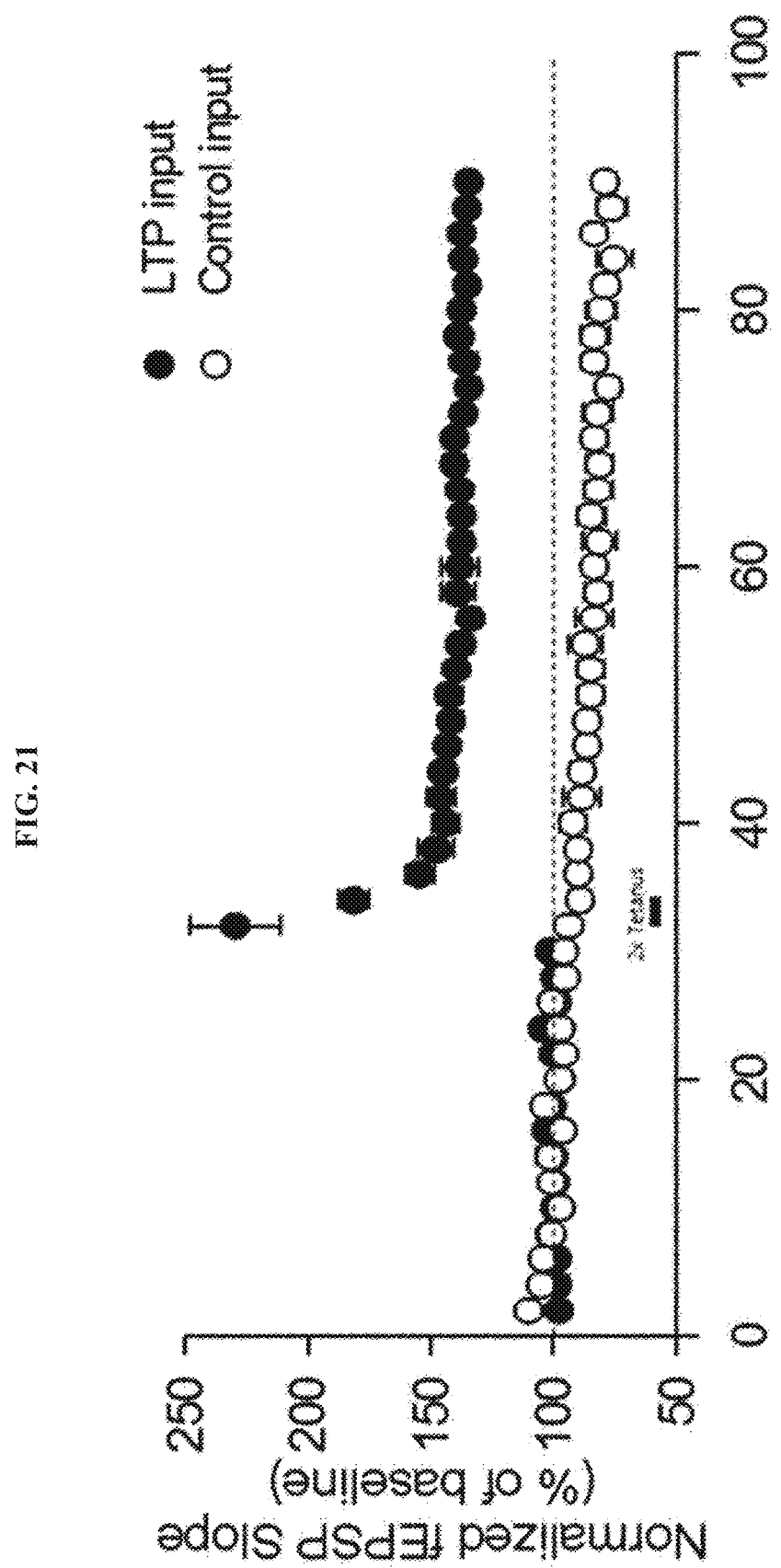
FIG. 21 is a graph showing results of an LTP induction experiment using a hippocampal slice of a mouse treated with only 80 nM of β-glucan according to Experimental Example 8.

As a result, LTP was induced in Sample 6 not treating with amyloid-β and β-glucan (FIG. 18), but LTP was not induced in Sample 7 treating with 500 nM of amyloid-β (FIG. 19). Meanwhile, LTP was also not induced in Sample 8 treating with 500 nM of amyloid-β and 80 μg/ml of β-glucan together (FIG. 20). In addition, LTP was induced in Sample 9 treating with only 80 μg/ml of β-glucan, similarly to Sample 6 (FIG. 21). That is, as described in Experimental Example 1, it was confirmed that the avenanthramide C according to the present invention could prevent amyloid-β inhibiting LTP, but β-glucan, which is one of the oat extracts, could not prevent amyloid-β inhibiting LTP.

Experimental Example 9: Effects of β-Glucan (β-Glucan) on Induced AD Mouse as a Comparative Example An LTP comparison experiment was performed on a hippocampal slice of an induced AD mouse using the same method as Experimental Example 3, except that β-glucan was used instead of avenanthramide C according to the present invention. The obtained results are illustrated in FIGS. 22A and 22B.

Figure 22A:
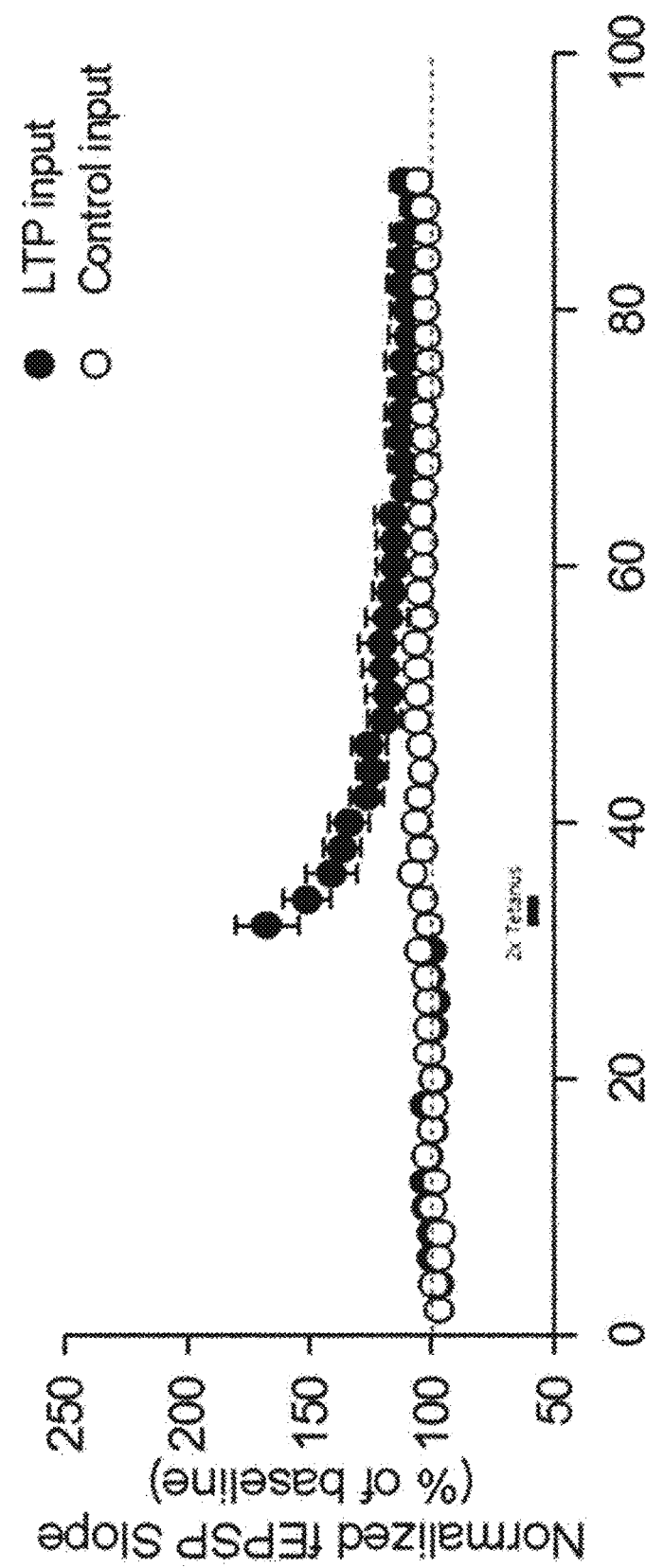
FIGS. 22A and 22B are graphs showing effects of β-glucan on the LTP in an induced AD mouse according to Experimental Example 9 (FIG. 22A: β-glucan-untreated hippocampal slice, and FIG. 22B: β-glucan-treated hippocampal slice).
Figure 22B:
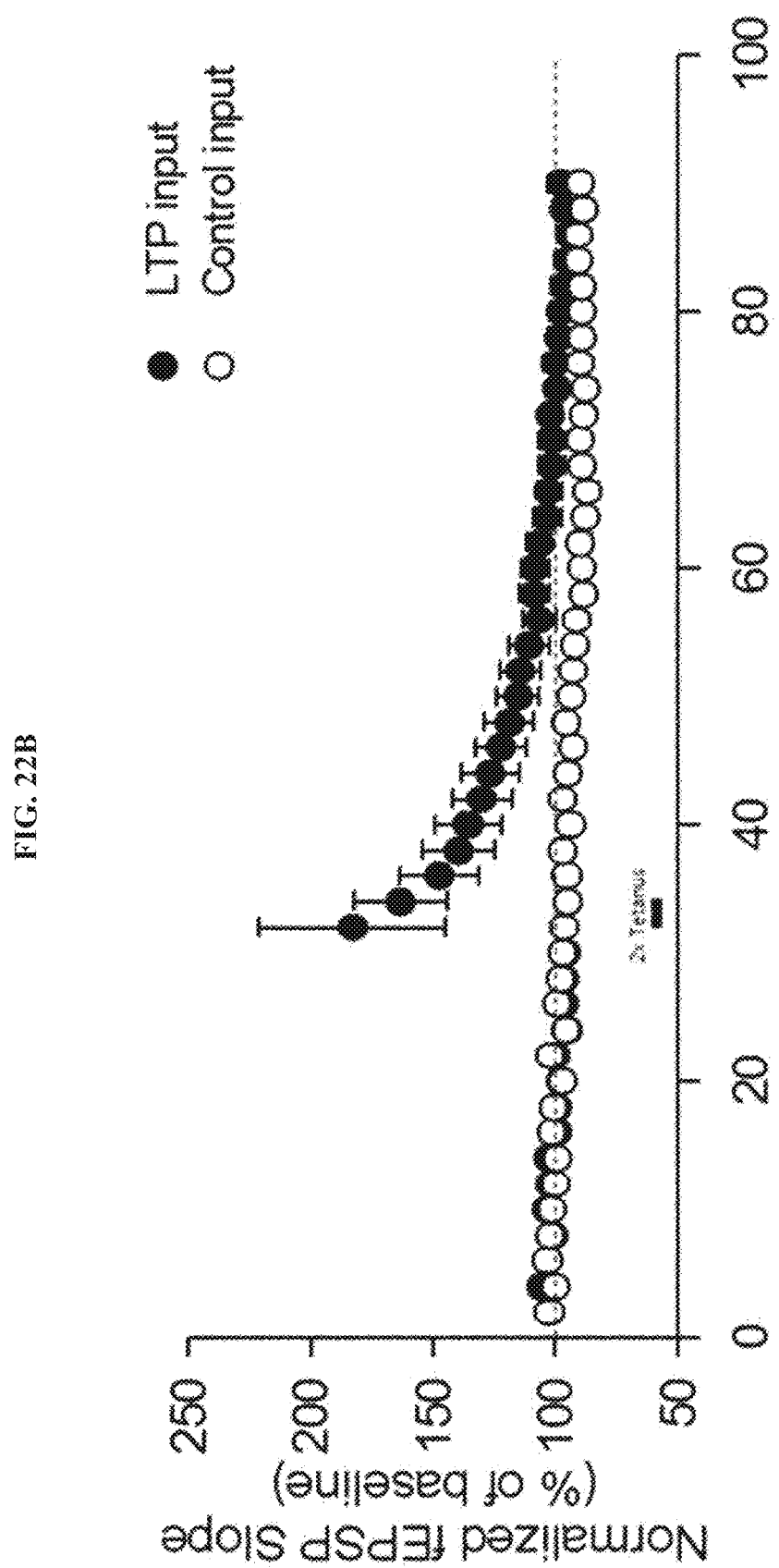

As can be seen from FIGS. 22A and 22B, it was confirmed that the induced AD mouse in a case of not performing any treatment failed to form the LTP (FIG. 22A), and the LTP was not induced similarly to the above case even when treating the sample with 80 μg/ml of β-glucan (FIG. 22B).

The present invention has been described above with reference to preferred embodiments thereof. It will be understood by a person having ordinary skill in the art to which the present invention pertains that various modifications and variations may be made therein without departing from the spirit and scope of the invention as defined by the appended claims. Therefore, the disclosed embodiments should be considered in an illustrative rather than a restrictive sense. The scope of the present invention is defined by the appended claims rather than by the foregoing description, and it should be interpreted that all differences within the scope of equivalents thereof are included in the present invention.

The avenanthramide C, which is the oat extract according to the present invention, is effective in inhibiting the activity of GSK3β induced by amyloid-β and inducing LTP inhibited by the accumulation of amyloid-β, thus may be helpfully used in the pharmaceutical composition and health functional food for prevention or treatment of Alzheimer's disease.

The invention claimed is:

1. A method for treatment of Alzheimer's disease, the method comprising:
   first-measuring at least one of an activity of glycogen synthase kinase-3β (GSK3β) and long-term potentiation (LTP) of a subject having the Alzheimer's disease;
   administering to the subject an amount of a composition, effective to reduce GSK3β activity and/or to induce long-term potentiation, including an oat extract having avenanthramide C represented by Formula 1 or Formula 2:

[Formula 1]
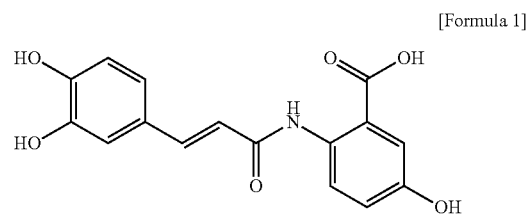 [SMILES: O=C(/C=C/c1ccc(O)c(O)c1)Nc1ccc(O)cc1C(=O)O]

[Formula 2]
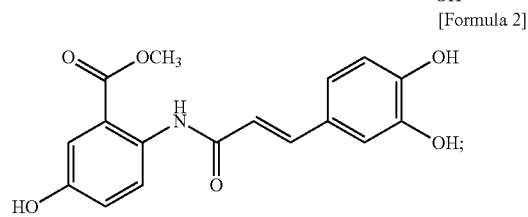

and
   after the administering, second-measuring said at least one of the activity of GSK3β and the long-term potentiation (LTP) to determine if the activity of GSK3β is reduced and/or the long-term potentiation (LTP) is induced in order to determine the treatment of the Alzheimer's disease.

2. The method of claim 1, wherein the avenanthramide C is included in an amount of 50 μM or more.

3. The method of claim 1, wherein a composition is a pharmaceutical composition.

4. The method of claim 3, wherein the pharmaceutical composition further comprises a carrier selected from the group consisting of lactose, dextrose, sucrose, sorbitol, mannitol, starch, acacia rubber, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, and mineral oil.

5. The method of claim 3, wherein the pharmaceutical composition further comprises at least one selected from the group consisting of a lubricant, a wetting agent, a sweetener, a flavoring agent, an emulsifier, a suspension, and a preserving agent.

6. The method of claim 3, wherein the pharmaceutical composition is administered by at least one selected from the group consisting of intravenous injection, subcutaneous injection, intramuscular injection, intraperitoneal injection, local administration, dermal administration, and nasal administration.

7. The method of claim 1, wherein a composition is included in a health functional food.

8. The method of claim 1, wherein the first-measuring comprising measuring the activity of glycogen synthase kinase-3β (GSK3β) of the subject having the Alzheimer's disease; and
  the second-measuring comprising measuring the activity of GSK3β to determine if the activity of GSK3β is reduced.

9. The method of claim 1, wherein the first-measuring comprising measuring the long-term potentiation (LTP) of the subject having the Alzheimer's disease; and
  the second-measuring comprising measuring the long-term potentiation (LTP) to determine if the long-term potentiation (LTP) is induced.

10. The method of claim 1, wherein the first-measuring comprising measuring the activity of glycogen synthase kinase-3β (GSK3β) and the long-term potentiation (LTP) of the subject having the Alzheimer's disease; and
  the second-measuring comprising measuring the activity of GSK3β and the long-term potentiation (LTP) to determine if the activity of GSK3β is reduced and the long-term potentiation (LTP) is induced.

* * * * *